US010089055B1

(12) United States Patent
Fryman

(10) Patent No.: US 10,089,055 B1
(45) Date of Patent: Oct. 2, 2018

(54) SYNCHRONIZED DISPLAY OF SCREEN CONTENT ON NETWORKED DEVICES

(71) Applicant: ICU Medical, Inc., San Clemente, CA (US)

(72) Inventor: Marshall Fryman, Lidenhurst, IL (US)

(73) Assignee: ICU Medical, Inc., San Clemente, CA (US)

( * ) Notice: Subject to any disclaimer, the term of this patent is extended or adjusted under 35 U.S.C. 154(b) by 0 days.

(21) Appl. No.: 15/861,204

(22) Filed: Jan. 3, 2018

Related U.S. Application Data

(60) Provisional application No. 62/610,742, filed on Dec. 27, 2017.

(51) Int. Cl.
*H04L 29/06* (2006.01)
*A61N 1/00* (2006.01)
*G06F 3/14* (2006.01)
*A61M 5/142* (2006.01)
*G06F 1/12* (2006.01)
*G16H 20/10* (2018.01)
*H04L 29/08* (2006.01)

(52) U.S. Cl.
CPC ............ *G06F 3/1423* (2013.01); *A61M 5/142* (2013.01); *G06F 1/12* (2013.01); *G16H 20/10* (2018.01); *A61M 2205/3584* (2013.01); *A61M 2205/50* (2013.01); *A61M 2205/502* (2013.01); *A61M 2205/52* (2013.01); *A61M 2205/6072* (2013.01); *H04L 67/12* (2013.01)

(58) Field of Classification Search
CPC ........ G06F 3/1423; G06F 1/12; A61M 5/142; A61M 2205/6072; A61M 2205/502; A61M 2205/52; A61M 2205/50; A61M 2205/3584; H04L 67/12; G16H 20/10
See application file for complete search history.

(56) References Cited

U.S. PATENT DOCUMENTS

| 8,121,857 | B2 | 2/2012 | Galasso et al. | |
|---|---|---|---|---|
| 9,138,526 | B2 | 9/2015 | Ware et al. | |
| 9,190,010 | B2 | 11/2015 | Vik et al. | |
| 9,943,269 | B2* | 4/2018 | Muhsin | G16H 40/63 |
| 2009/0077248 | A1* | 3/2009 | Castellucci | H04L 12/14 709/229 |
| 2009/0177248 | A1* | 7/2009 | Roberts | G06F 19/327 607/60 |
| 2009/0177769 | A1* | 7/2009 | Roberts | G06F 19/327 709/224 |
| 2013/0318158 | A1* | 11/2013 | Teng | H04L 67/42 709/203 |

(Continued)

FOREIGN PATENT DOCUMENTS

WO    WO 2017051271 A1    3/2017

*Primary Examiner* — Abdullahi E Salad
(74) *Attorney, Agent, or Firm* — Knobbe, Martens, Olson & Bear, LLP

(57) ABSTRACT

A system configured to synchronize the displays of multiple infusion pumps is provided. In some embodiments, the system includes a plurality of infusion pumps in communication with a server. An individual infusion pump synchronizes its internal clock by communicating with the server. Based on the synchronized internal clock, the infusion pump determines the current time, calculates a parameter based on the current time, and causes screen content corresponding to the calculated parameter to be displayed.

16 Claims, 7 Drawing Sheets

(56) References Cited

U.S. PATENT DOCUMENTS

| | | | |
|---|---|---|---|
| 2014/0267563 A1* | 9/2014 | Baca | H04N 21/4307 348/14.08 |
| 2015/0033073 A1* | 1/2015 | Yang | G06F 11/1438 714/15 |
| 2016/0042264 A1 | 2/2016 | Borges et al. | |
| 2016/0110088 A1 | 4/2016 | Vik et al. | |
| 2017/0043089 A1* | 2/2017 | Handler | A61M 5/1723 |

* cited by examiner

US 10,089,055 B1

SYNCHRONIZED DISPLAY OF SCREEN CONTENT ON NETWORKED DEVICES

INCORPORATION BY REFERENCE TO ANY PRIORITY APPLICATIONS

This application claims priority to U.S. Provisional Application No. 62/610,742, filed on Dec. 27, 2017 and titled "SYNCHRONIZED DISPLAY OF SCREEN CONTENT ON NETWORKED DEVICES." Any and all applications for which a foreign or domestic priority claim is identified in the Application Data Sheet as filed with the present application are hereby incorporated herein by reference in their entirety under 37 CFR 1.57.

TECHNICAL FIELD

This disclosure relates to the field of networked devices, and particularly to techniques for synchronizing the screen content displayed on a plurality of networked devices.

BACKGROUND

Networked devices capable of displaying information are commonplace in modern network environments. Such networked devices may each include a display screen configured to display information generated by the networked device such as a status of the networked device, an error encountered by the networked device, etc. Based on the information displayed on the display screens, users may determine whether any action needs to be taken with respect to the networked devices.

SUMMARY

Various techniques for providing a synchronized display of screen content on a plurality of networked devices are described herein. Although many of the examples are described in the context of a hospital environment, the techniques described herein can be applied to any network environment including multiple networked devices. The networked devices described herein may include infusion pumps, other medical devices, or non-medical devices, or any combination thereof. The screen content described herein may be drug delivery metrics, other medical device screen content, other display screen content, or any combination thereof. The synchronization of the screen content displayed on multiple networked devices may be performed without having a centralized server communicate with each networked device to coordinate the content and/or timing of the displayed screen content. In some cases, synchronization of the screen content displayed on multiple networked devices is performed based on synchronizing the internal clocks of the respective networked devices with a reference time. In other cases, synchronization of the screen content displayed on multiple networked devices occurs without synchronizing the internal clocks of the respective networked devices and without utilizing a centralized server to synchronize the displays of the multiple networked devices. These and other embodiments are described in greater detail below with reference to FIGS. 1-7.

BRIEF DESCRIPTION OF THE DRAWINGS

The embodiments described herein are illustrated by way of example, and not by way of limitation, in the figures of the accompanying drawings in which like references indicate similar elements.

DETAILED DESCRIPTION

Introduction

Figure 1:
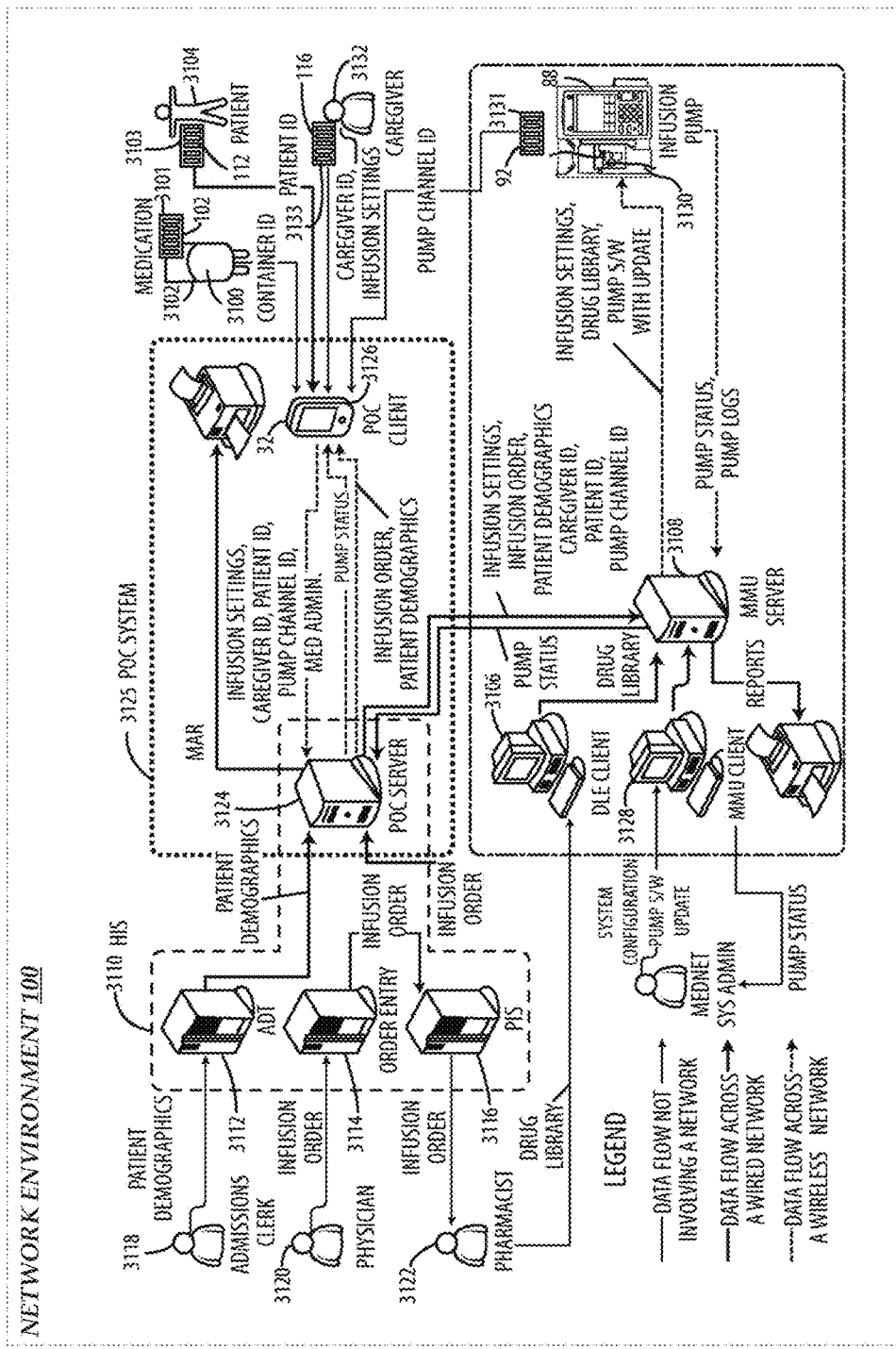
FIG. 1 is a schematic diagram of an example network environment including one or more networked devices in accordance with aspects of this disclosure.

A network environment may include multiple electronic devices. One example of such an environment is a hospital network environment, where a centralized server communicates with multiple medical devices such as patient care monitors and infusion pumps. In the hospital network environment, the centralized server may control how the medical devices in the hospital network environment operate and what kind of information is presented via the medical devices. For example, several patients may share a single room in a hospital, and the patients may each be assisted by a number of medical devices. Such medical devices may each include a display screen through which various physiological metrics, warnings, measurements, and other information may be presented to the caregiver or patient.

As the number of such networked devices displaying and updating screen content increases, viewing and understanding the displayed information becomes more difficult. For example, a caregiver may wish to quickly scan an array of 10 infusion pumps to determine whether the infusion pumps are functioning properly, infusing the medications at the correct rate, how much time it will be until the medication delivery is complete, etc. However, if the 10 infusion pumps are each cycling through multiple metrics on their displays (e.g., rate, dose, time remaining, volume infused, volume to be infused, etc.) at different times, the caregiver may find that distracting and inefficient. As another example, a system administrator may wish to scan an array of monitors to ensure that all of the servers are performing properly. However, if the monitors are cycling through different server statistics out of sync, it may be difficult for the system administrator to gather the necessary information from the monitors. Thus, an improved method of synchronizing the displays of such networked devices is desired.

Synchronizing Screen Content Displayed on Networked Devices

In some implementations, the networked devices described above (e.g., infusion pumps, monitors, etc.) in a network environment cause their respective screen content to be changed in response to a signal received from a server. For example, the server may transmit a "heartbeat" signal to each networked device every 15 seconds, indicating that the networked device should change the displayed content or switch to the next content in a given display order. Such a signal from the server may also indicate which content the networked device should display (e.g., by including a content identifier in the signal transmitted to the networked device). In such implementations, the signal would be received and processed by the individual networked devices at approximately the same time, and the content displayed on their displays would be synchronized as a result.

However, such use of heartbeat signals can consume valuable network resources (e.g., bandwidth) and overwhelm the network, especially if the network includes a large number of such networked devices. Further, processing such heartbeat signals from the server may require a sophisticated processor on the networked device and/or consume valuable processing power. In view of these technical considerations, in some cases, it may be beneficial to display and cycle through screen content without relying on such a heartbeat signal. In another implementation, the screen content may be displayed based on an internal clock maintained by the individual networked devices and without communicating with the server each time new screen content needs to be displayed. In such implementations, the amount of data transmitted across the network environment may be significantly reduced and valuable network resources and/or processing power can be preserved for other uses. The techniques for synchronizing the screen content displayed on networked devices in this manner are described in greater detail below with reference to FIGS. 2-7.

In yet another implementation, the individual networked devices locally store a fixed schedule of which metric to display at what time. In such an implementation, a networked device may store a table that specifies, for each controlling variable (e.g., clinical care area of an infusion pump), which metric should be displayed at a given time of day. For example, the table may specify that for networked devices in the intensive care unit should display metric #1 for the first 10 minutes of every hour, metric #2 for the second 10 minutes, metric #3 for the third 10 minutes, and so on, and for networked devices in the operating room should display metric #3 for the first 30 minutes of every hour, and metric #4 for the second 30 minutes of every hour. As another example, the table may specify, for each 5-second interval in the 24 hours of a given data, the metric to be displayed for the 5-second interval. However, locally storing such a table would consume a large amount of memory or disk space, which may not be desired for networked devices having limited memory/storage. Further, even if such a table is accessed from a remote network location, accessing the table over the network can consume valuable network resources (e.g., bandwidth) and overwhelm the network, especially if the network includes a large number of such networked devices. As discussed above, displaying the screen content based on an internal clock maintained by the individual networked devices and without storing or accessing large amounts of data specifying the screen content to be displayed at any given interval may provide certain technical benefits such as reducing the amount of storage space needed and/or data transmitted across the network environment and allowing valuable storage/network resources to be preserved for other uses.

With reference to FIG. 1, an example network environment in which one or more of the display synchronization techniques of the present disclosure may be utilized is described. Following the discussion of FIG. 1, specific details of the various embodiments of the present disclosure are described with reference to FIGS. 2-7.

Overview of Example Network Environment

FIG. 1 illustrates one embodiment of a system for administering medication via an infusion pump in a network environment 100. The medication management system (MMS) shown in FIG. 1 includes a medication management unit (MMU) server 3108 and a medical device, such as infusion pump 3130, operating in conjunction with one or more information systems or components of a hospital environment.

Intravenous (IV) fluid(s) and/or medication(s) 3100 in containers 3102 may be administered to a patient 3104 using the system shown in FIG. 1. Although the system shown in FIG. 1 utilizes barcodes and a barcode reader as apparatus to input and read machine-readable information, those skilled in the art will appreciate that other apparatus for reading or inputting information may be utilized. Moreover, a point of care (POC) client 3126 may include an identification receiver 32 adapted to recognize such indicia may be provided in the MMS.

In certain aspects, the IV fluids and/or medications 3100 in container 3102 may be provided with new or supplemental labels with a unique infusion order identifying barcode by a pharmacist according to certain hospital practices. Specifically, drug container specific identification information, such as barcoded information on the container 3102 may include patient identification information, medication identification information, universal identification information, medical device delivery information, and/or medication order information. The IV fluids and/or medications 3100 in barcode-identified containers 3102 may be supplied to hospitals by various vendors, with preexisting unique barcode identifiers, which include medication information and other information, such as a National Disease Center (NDC) code, expiration information, drug interaction information, and the like.

In some aspects of the disclosure, the universal identification information on the container 3102 may be a unique medication order identifier that, by itself, identifies the order associated with the container. In other aspects, the identification information on the container 3102 may be a composite patient/order code that contains both a patient ID (such as a medical record number) and an order ID unique only within the context of the patient. In certain aspects, the identification information on the container 3102 may include a medication ID. The system identified in FIG. 1 may include a drug library editor (DLE) client 3106, such as a notebook, desktop or server computer. The DLE client 3106 may include DLE software. As described above, the MMU server 3108 may have MMU software that is installed and runs on the MMU server 3108. The drug library and other databases may be stored on the MMU server 3108, on a separate server, and/or in remote locations.

Hospital information systems (HIS) 3110 may include one or more computers connected by cabling, interfaces, and/or Ethernet connections. Alternatively, wireless connections and communications may be used in whole or in part. Servers provide processing capability and memory for storage of data and various application programs or modules, including but not limited to an admissions-discharge-and-transfer (ADT) module or computer 3112, a computerized physician order entry (CPOE) module or computer 3114, and a pharmacy information system (PIS) module or computer 3116. Hospital personnel, such as admission clerks 3118, physicians 3120, and pharmacists 3122, respectively, may be authorized to access these modules through client workstations connected to the servers in order to enter data, access information, run reports, and complete other tasks.

In the embodiment shown in FIG. 1, the HIS 3110 may also include a POC system 3125 including a server or POC computer 3124 (sometimes referred to as a barcode point of care server or computer), or the POC computer 3124 may be separate from the HIS 3110. The POC computer 3124 may act as a part of the POC system 3125 (sometimes referred to as the barcode point of care system or BPOC) and may be able to wirelessly communicate through a plurality of wireless communication nodes located throughout the hospital, utilizing a wireless communications protocol, such as IEEE 801.11, IEEE 802.11, or Bluetooth. The POC computer 3124 may communicate wirelessly with a portable thick client, POC client 3126, carried by a caregiver. The POC client 3126 may be a personal digital assistant (PDA) that includes significant memory, display, and processing capabilities. The POC client device may execute a variety of programs stored in its memory in some degree independently of the POC computer 3124.

In one embodiment of FIG. 1, the MMU server 3108 may be hard-wired to the DLE client 3106 and to a MMU client 3128. Alternatively, the MMU and DLE client functions may be combined onto a single client computer/workstation or may reside together with the MMU server 3108 on a single combined MMU/DLE server. The MMU server 3108 may reside in a location remote from the patient's room or treatment area. For instance, the MMU server 3108 may reside in a secure, climate controlled information technology room with other hospital servers, and computer equipment and its client terminals may be located in the pharmacy, biomedical engineering area, nurse station, or ward monitoring area. One MMU server 3108 may monitor, coordinate, and communicate with many infusion pumps 3130. For example, in one embodiment, the MMU software running on the MMU server 3108 may support up to one thousand infusion pumps concurrently.

In embodiment of FIG. 1, the POC client 3126 in the POC system 3125 may communicate through the POC server 3124 with the MMU server 3108. The MMU server 3108 may interface or communicate wirelessly with the infusion pump 3130 through the same wireless nodes utilized by the POC system 3125 and a connectivity engine and antenna on or in the infusion pump 3130. Communication between the infusion pump 3130 and the POC client 3126 may take place through the MMU server 3108 and POC server 3124. The MMU server 3108 may store in an associated memory both the logical ID and the network ID or Internet Protocol (IP) address of the infusion pump(s) 3130, such that only the MMU server 3108 may communicate in a direct wireless manner with the infusion pump 3130. Alternatively, the MMU server 3108 may provide the IP address and other information about the infusion pump 3130 to the POC system 3125 to facilitate direct communication between the POC system 3125 and the infusion pump 3130.

Upon admission to the hospital, the admission clerk 3118 or similar personnel may enter demographic information about each patient 3104 into an associated memory of the ADT module or computer 3112 of an HIS database stored in an associated memory of the HIS 3110. Each patient 3104 may be issued a patient identification wristband, bracelet, or tag 112 that may include an identifier 3103, such as a barcode or RFID tag, identifying the patient. The wristband, bracelet, or tag 112 may also include other information, in machine readable or human-readable form, such as the name of the patient's doctor, blood type, allergies, and the like.

The patient's doctor 3120 may prescribe medical treatment by entering a medication order into the CPOE module or computer 3114 within the HIS 3110. The medication order may specify a start time, stop time, a range of allowable doses, physiological targets, route, and site of administration. In the case of an order for infusion of fluids or medication, the order may be written in various formats, and may include the patient's name, patient ID number, a unique medication order or prescription number, a medication name, medication concentration, a dose or dosage, frequency, and/or a time of desired delivery. This information may be entered into the memory of the CPOE module or computer 3114, and may be stored in a memory associated with at least the POC server 3124.

The medication order may also be delivered electronically to the PIS module or computer 3116 in the pharmacy and may be stored in an associated memory. The pharmacist 3122 may screen the prescribed order, translate it into an order for dispensing medication, and prepare the medication or fluids with the proper additives and/or necessary diluents. The pharmacist 3122 may prepare and affix a label 102 with drug container specific identifying information 3101 to the medication or drug container 3102. The label may include in machine-readable and/or human-readable form medical device specific delivery information including but not limited to the dispense ID number, patient ID, drug name, drug concentration, container volume, volume-to-be-infused ("VTBI"), rate, duration, and the like. Only two of the three variables VTBI, rate, and duration may be defined as the third may be calculated when the other two are known. The labeled medication may be delivered to a secure, designated staging location or mobile drug cart on the ward or floor near the patient's room or treatment area. The medication order pending dispensing or administration may be posted to a task list in the HIS 3110 and POC system 3125 and stored in an associated memory.

The caregiver 3132 (e.g., a nurse) may use the identification receiver 32 associated with the POC client 3126 to scan his/her caregiver identification badge 116 and enter a password, which logs the caregiver into the system and authorizes the caregiver to access a nurse's task list from the POC system 3125 through the POC client 3126. The caregiver 3132 may view from the task list that IV drugs are to be administered to certain patients 3104 in certain rooms. The caregiver 3132 obtains the necessary supplies, including medications, from the pharmacy and/or a staging area in the vicinity of the patient's room.

The caregiver 3132 may take the supplies to a patient's bedside, turn on the infusion pump 3130, verify that the network connection icon on the infusion pump 3130 indicates a network connection (for example, a wireless connection such as Wi-Fi or the like) is present, select the appropriate clinical care area (CCA) on the infusion pump 3130, and mount the IV bag, container, or vial 3102 and any associated tube set as required in position relative to the patient 3104 and infusion pump 3130 for infusion. Another connection icon on the infusion pump 3130 or pump user interface screen can indicate that a wired or wireless connection to the MMU server 3108 is present. Using the identification receiver/reader integral to the POC client 3126, the caregiver 3132 may scan the barcode on the patient's identification wristband, bracelet, or tag 112 or other patient identification device. A task list associated with that particular patient may appear on the POC client 3126 screen. The task list, which may also include orders to give other forms of treatment or medication by other routes (oral, topical, etc.), may be obtained from the HIS 3110 via the POC server 3124 and communicated wirelessly to the POC client 3126. In one embodiment, the list is generated by matching the scanned patient ID with the patient ID for orders in memory within the POC server 3124. In another embodiment, the order information may be obtained by scanning the drug container specific identification information for associated orders in memory within the POC server 3124, through the following step(s).

The caregiver 3132 may scan the medication barcode label 102 containing medication container specific identification information 3101 on the medication container 3102 with the POC client 3126. The POC client 3126 may highlight the IV administration task on the task list and send the scanned medication container specific identification information, such as dispense ID information, from the medication container 3102, to the POC server 3124. The POC server may use the medication container specific identification information to pull together the rest of the order details and send them back to the POC client 3126. The POC client 3126 may then display an IV Documentation Form on its screen. One side of the IV Documentation Form screen may show the order details as "ordered" and the other side may be reserved for a status report from the infusion pump 3130. The status report from the infusion pump 3130 may be transmitted to the POC client 3126 through the POC server 3124 and MMU server 3108. The lower portion of the IV Documentation Form screen may provide the caregiver 3132 with instructions (like to scan the infusion pump 3130 barcode) or identify whether the pump is running or stopped.

The caregiver 3132 may then scan the barcode label 92 associated with the infusion pump 3130 (or pump channel if the pump is a multi-channel pump). The barcode label 92 may contain medical device specific identification information 3131, such as the logical name and/or logical address of the device or channel. The POC system 3125 then automatically bundles the information into a program pump request containing the "order details" and in one embodiment, without further interaction with the caregiver 3132, transmits this information to the MMU server 3108.

The program pump request may include at least some of the following information (in HIS/POC system format): a Transaction ID, which may include a Logical Pump ID, a Pump Compartment, a Pump Channel ID, a Reference Device Address, a Caregiver ID, a Caregiver Name, a Patient/Person ID (HIS identifier), a Patient Name, a Patient Birth Date & Time, a Patient Gender, a Patient Weight, a Patient Height, and an Encounter ID which may include a Room, a Bed, and a Building (including CCA). The program pump request may also include Order Information or "order details", including an Order ID, a Start Date/Time, a Stop Date/Time, a Route of Administration, a Rate, a Duration of Infusion (Infuse Over), a Total Volume to be Infused (VTBI), an Ad Hoc Order Indicator, and Ingredients including HIS Drug Name or HIS Generic Drug Name, HIS Drug Identifier or HIS Generic Drug ID, Rx Type (Additive or Base), Strength w/units, and Volume w/units. The program pump request may further include Patient Controlled Analgesia (PCA) Orders Only information, such a PCA Mode-PCA only, Continuous only, or PCA and Continuous, a Lockout Interval (in minutes), a PCA Continuous Rate, a PCA Dose, a Loading Dose, a Dose Limit, a Dose Limit Time w/units, a Total Volume in vial or syringe, and Order Comments.

The MMU server 3108 may map or convert the wide range of expressions of units allowed by the HIS 3110 or POC system 3125 for POC client 3126 requests into the much more limited set of units allowed in the MMU server 3108 and infusion pump 3130. For example, the POC client 3126 request may express "g, gm, gram, or grams" whereas the MMU server 3108 and/or infusion pump 3130 may accept "grams" only. Infusion pump 3130 delivery parameters or infusion pump 3130 settings are mapped or converted from corresponding order information or "order details" of the program pump request.

The MMU server 3108 may store in an associated memory a mapping or translation table that keep track of the logical ID, serial number or other identifier of an infusion pump 3130 and the corresponding current network (static or dynamic) address (Internet Protocol (IP) address) or ID of the infusion pump 3130 on the network, which in this example is a wireless network. The MMU server 3108 may be able to translate or associate a given identifier of the infusion pump 3130 with its network address in the translation table and provide the network IP address to the requesting POC system 3125 or device. The MMU server 3108 may also store in an associated memory and/or look up the drug library applicable to the scanned infusion pump 3130 and/or convert the Drug ID and Strength from the pump program request into an index number of the medication at the desired strength or concentration from the drug library. The duration of the infusion may come from the POC system 3125 in hours and minutes and may be converted to just minutes for the infusion pump 3130 to recognize it. Volume or VTBI may be rounded to provide a value-specific and infuser-specific number of digits to the right of the decimal point. Units (of drug) may be converted to million units where appropriate. Patient weight may be converted and either rounded according to infuser-specific rules or not sent to the infuser.

Once the MMU server 3108 transforms the information from the program pump request into infusion pump settings or delivery parameters and other information in a format acceptable to the infusion pump 3130, the MMU server 3108 may wirelessly download a command message to the infusion pump 3130. If the infusion pump 3130 is not already equipped with the latest appropriate version of the hospital-established drug library, the MMU server 3108 may also automatically download a drug library to the infusion pump 3130. The hospital-established drug library may be maintained in a separate process undertaken by the biomedical engineer or pharmacist 3122 to place limits on the programming of the infusion pump 3130, as well as other infusion pump operating parameters such as default alarm settings for air in the line, occlusion pressure, and the like. The drug library may set up acceptable ranges or hard and/or soft limits for various drug delivery parameters in the infusion pump 3130.

The MMU server 3108 may also download to the infusion pump new versions, patches, or software updates of the infusion pump's internal operating system software. The infusion settings or delivery parameters and other information from the MMU server 3108 may be entered into the memory of the infusion pump 3130 and the infusion pump 3130 settings may automatically populate the programming screen(s) of the infusion pump 3130, just as if the caregiver 3132 had entered the information and settings manually. The infusion pump 3130 screen may populate with the name of the drug and drug concentration based on the drug library index number, patient weight, rate, VTBI, and/or duration. Further, the MMU server 3108 may transmit one or more synchronization signals or screen content display rules/parameters to the infusion pump 3130, as described in greater detail below with reference to FIGS. 2-7. A return message of confirmation signal may be sent to the MMU server 3108 by the infusion pump 3130 to indicate that the command message has been received. At this point, if necessary, the caregiver 3104 may manually enter any additional infusion settings or optional information that was not included in the command message.

The infusion pump 3130 may then prompt the caregiver 3132 to start the infusion pump 3130 by pressing the start button. When the caregiver 3132 presses the start button, a confirmation screen with the infusion settings programmed may be presented for confirmation and an auto-program acknowledgment message can be sent to the MMU server 3108 to forward without request (i.e., pushed in a near real-time manner) or provide to the POC system 3125 when requested or polled. When the caregiver 3132 presses the button to confirm, the infusion pump 3130 may begin delivering fluid according to the programmed settings. The infusion pump 3130 may send a status message to the MMU server 3108 indicating that the infusion pump 3130 was successfully auto-programmed, confirmed and started by the caregiver 3132, and is now delivering fluid. This information may also be displayed at the infusion pump. The MMU server 3108 may continue to receive logs and status messages wirelessly from the infusion pump 3130 periodically as the infusion progresses or when alarms occur.

The MMU server 3108 may report a portion of the initial status message to the POC client 3126 through the POC server 3124 (in MMU format) to indicate that the infusion pump 3130 has been auto-programmed and the caregiver 3132 has confirmed the settings. The MMU server 3108 may communicate to the POC system 3125 and/or at the infusion pump 3130 the actual Rate, VTBI, and Duration. A notation at the bottom of the screen of the POC client and/or the infusion pump may indicate that the infusion pump 3130 is running. The infusion pump 3130 may compare and give a visual, audio, or other type of affirmative signal if the pump information matches or acceptably corresponds with the ordered information. An initial determination of whether the pump information matches the order may be done in the MMU server 3108 and communicated to the POC client 3126 through the POC server 3124. Alternatively, the POC server 3124 or the infusion pump 3130 may make the necessary comparisons. If the pump information does not match the order, the infusion pump 3130 at the display 88 may output a visual, audio, or other type of negative signal, which may include an error message.

The caregiver 3132 may be prompted to review and press a save button on the infusion pump 3130 if the order has been begun as desired or any variations are acceptable. The MMU server 3108 may receive status, event, differences, and variation information from the infusion pump 3130 and pass such information to the POC system 3125. In a separate subsequent step, the nurse may electronically sign the record and presses a send button on the POC client POC client 3126 to send the information to the patient's electronic medication record (EMR) or medication administration record (MAR).

Other Environments

FIG. 1 illustrates one example environment in which the various display synchronization techniques of the present disclosure may be utilized. However, the embodiments described herein are not limited to such an environment, and may be applied to any network environment including one or more networked devices having a display. An example system that may be implemented in one or more of such network environments to provide synchronized display of screen content is described below with reference to FIG. 2.

System Overview

Figure 2:
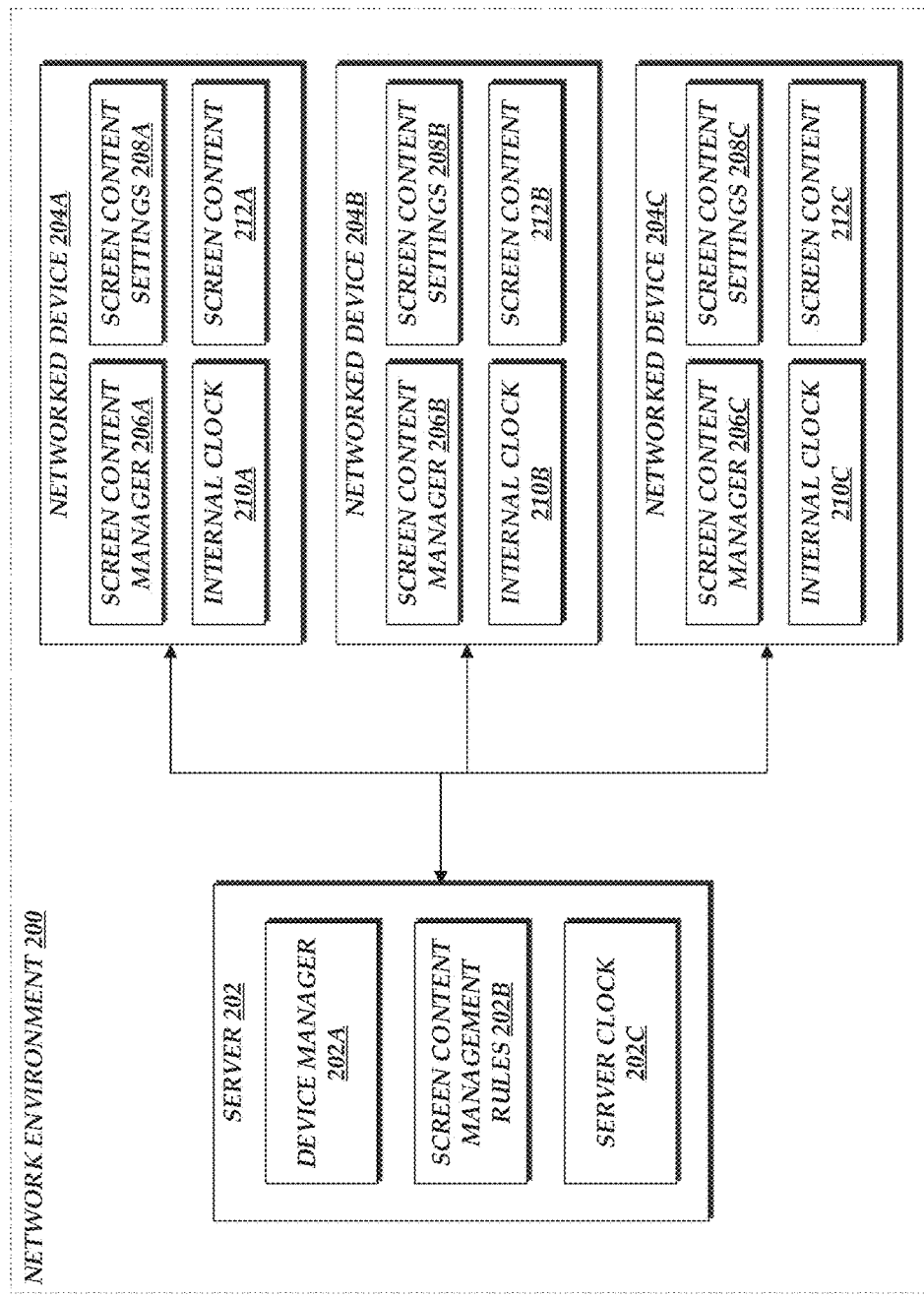
FIG. 2 is a block diagram illustrating components of an example network environment in accordance with aspects of the present disclosure.

FIG. 2 is a block diagram of an example network environment 200, which includes an arrangement of computer hardware and software components that may be used to implement aspects of the present disclosure. The network environment 200 may include many more (or fewer) elements and/or sub-elements than those shown in FIG. 2. It is not necessary, however, that all of these elements be shown in order to provide an enabling disclosure. As illustrated in FIG. 2, the network environment 200 includes a server 202 and networked devices 204A-C (collectively referred to herein as networked device 204 or networked devices 204).

Server

The server 202 includes a device manager 202A configured to manage the networked devices 204, screen content management rules 202B governing how screen content displayed and changed on networked devices 204, and a server clock 202C configured to maintain a reference time for the network environment 200. The server 202 may include additional components not illustrated in FIG. 2. In some embodiments, the server 202 may omit one or more of the components illustrated in FIG. 2.

The device manager 202A may be a software module or application that is configured to perform certain control functions with respect to the networked devices 204. In some embodiments, the device manager 202A is a computing device including circuitry for executing computer instructions and performs one or more functions described herein (e.g., sending clock information to the individual networked devices, sending screen content settings or parameters to the individual networked devices, etc.). The device manager 202A generally initiates, performs, coordinates, and/or controls various management operations with respect to the networked devices 204.

The screen content management rules 202B may include one or more parameters to be used to control the screen content display at the individual networked devices. For example, the screen content management rules 202B may specify which information, metrics, or other screen content should be displayed and the order in which such information should be displayed on the individual networked devices. In a clinical care setting, the screen content management rules 202B may specify that the networked devices in Clinical Care Area X (e.g., emergency room) should display metrics A, B, and D for 5 seconds each (e.g., display A for 5 seconds, then display B for 5 seconds, then display D for 5 seconds, and then display A again for 5 seconds, etc.), and that networked devices in Clinical Care Area Y (e.g., intensive care unit) should display metrics A and E, 10 seconds each (e.g., display A for 10 seconds, then display E for 10 seconds, then display A again for 10 seconds, etc.).

The server clock 202C may be a clock that keeps track of a reference time to which the individual networked devices in the network environment are synchronized. For example, the reference time according to the server clock 202C may be transmitted to the networked devices 204 according to a schedule (e.g., periodically), based on a user input received by the server 202, or in response to a request received from the individual networked devices 204. For example, the screen content manager 206 may be configured to request the reference time from the server 202 according to a schedule (e.g., every 24 hours, every week, every month, etc.) or based on a user input received by the networked device 204.

Although the server 202 is illustrated in FIG. 2 as including the server clock 202C that keeps track of the reference time for the networked devices 204, in other embodiments, the network environment 200 may not include the server 202, and the networked device 204 may synchronize or calibrate its internal clock by communicating an entity outside the network environment 200. In some cases, the networked device 204 does not synchronize or calibrate its internal clock by communicating with another entity.

Networked Device

The networked device 204A includes a screen content manager 206A, screen content settings 208A, an internal clock 210A, and screen content 212A. The networked device 204B includes a screen content manager 206B, screen content settings 208B, an internal clock 210B, and screen content 212B. The networked device 204C includes a screen content manager 206C, screen content settings 208C, an internal clock 210C, and screen content 212C. The networked device 204 may include additional components not illustrated in FIG. 2. For example, the networked device 204 may include one or more components configured to perform a medical function such as delivering a drug to a patient or monitoring such delivery. In some embodiments, the networked device 204 may omit one or more of the components illustrated in FIG. 2.

The screen content manager 206 may be a software module or application that is configured to perform certain functions described herein as being performed by the networked devices 204. In some embodiments, the screen content manager 206 includes circuitry for executing computer instructions and performs one or more functions described herein.

The screen content settings 208 may include one or more parameters to be used to control the screen content display at the individual networked devices. Such parameters may be received from the server 202 or inputted at the networked device 204.

The internal clock 210 may be a clock maintained by the networked device 204, and the internal clock 210 in the individual networked devices may periodically be synchronized with the server clock 202C at the server 202. Such synchronization may occur according to a schedule (e.g., periodically), based on a user input received by the server 202, or based on a user input received by the networked device 204. For example, the screen content manager 206 may be configured to request the reference time from the server 202 according to a schedule (e.g., every 24 hours, every week, every month, etc.) or based on a user input received by the networked device 204.

In some embodiments, the internal clock 210 of the individual networked devices are synchronized with the server clock 202C dynamically based on how quickly the internal clock 210 becomes out of sync. For example, when the networked device 204A sends a clock synchronization request to the server 202, and the server 202 transmits a clock synchronization signal to the networked device 204A, the networked device 204A may update the internal clock 210A using the received clock synchronization signal. In some cases, instead of updating the internal clock 210A, the networked device 204 may calculate an offset between the server clock 202C and the internal clock 210A, and apply the offset when determining the current time (e.g., for identifying the screen content to be displayed). Additionally, the networked device 204A may calculate the difference between the time according to the internal clock 210A prior to the synchronization and the time indicated by the clock synchronization signal (or the time according to the server clock 202C). If the difference is greater than a threshold amount (e.g., 1 second, 5 seconds, 10 seconds, etc.), the networked device 204A may increase the frequency at which the networked device 204A requests synchronization of the internal clock 210A with the server clock 202C. For example, if the time elapsed between the last two synchronizations was 5 days, and the time difference was 2 seconds, the networked device 204A may request the next synchronization 2 or 3 days (e.g., less than 5 days) after the most recent synchronization. If the networked device 204A determines that, after synchronizing the clocks 2 days after the most recent synchronization, the time difference fell below the threshold amount of drift (e.g., 1 second), then the networked device 204A may continue to request synchronization every 2 days. If the time difference was still above the threshold amount of drift, the networked device 204A may further increase the synchronization frequency (e.g., to 1 day, to 12 hours, or some other duration less than 2 days).

In some embodiments, the individual networked devices each have a different synchronization schedule. For example, the networked device 204A may request synchronization every 2 days, the networked device 204B may request synchronization every 3 days, and the networked device 204C may request synchronization every 5 days. In such cases, the time at which the individual networked devices are synchronized with the server clock 202C may not be identical or may not overlap with each other. In some embodiments, the schedule at which the individual networked devices are synchronized with the server clock 202C is non-periodic. In some cases, the threshold amount of drift is set to a value that is substantially lower than the content display period (e.g., 1%, 5%, 10%, etc.). For example, if the metrics are rotated every 10 seconds, the difference of 0.1 second among the display times of the networked devices may be acceptable or negligible (e.g., the networked device 204A switching from "volume infused" to "rate" at 11:20:00.01 in reference time and the networked device 204B switching from "volume infused" to "rate" at 11:20:00.00 in reference time, where the networked devices continue to display "rate" until 11:20:10.01 and 11:20:10.00 in reference time, respectively). Although some examples of clock synchronization were described as being requested by the networked devices, in other examples, the clock synchronization may be requested by the server 202.

Time according to the internal clocks of the individual networked devices may be measured from the same reference point. For example, each internal clock is configured to output a current time indicative of the number of seconds elapsed since year 1900 (e.g., over 3 million seconds). In some embodiments, the reference point shared by the internal clocks is periodically updated so that time-based calculations involve smaller numbers. Although some clock synchronization techniques described with reference to FIG. 2 uses a server clock 202C, in some implementations, the internal clocks 210 may be synchronized using a network time protocol (NTP). In such implementations, the networked devices 240 may communicate with an NTP server to update their internal clocks 210 (e.g., periodically or aperiodically). Alternatively or additionally, the networked devices 240 may synchronize the internal clocks 210 using an atomic clock.

The screen content 212 may include one or more metrics calculated or maintained by the individual networked devices. For example, such metrics may include the volume of the medication infused so far, the volume of the medication to be infused, the rate at which the medication is being infused, and the like. The metrics may also include any other metrics or parameters described herein.

Centralized Display

In some embodiments, the network environment 200 of FIG. 2 may include a centralized display that can display the screen content associated with multiple networked devices 204. For example, the screen of the centralized display may be divided into multiple portions that can each display the screen content associated with a specific networked device 204. In some cases, the multiple networked device 204 whose screen content is displayed on the centralized display may be from multiple geographic locations (e.g., two or three different CCAs) and as a result may be configured to cycle through different metrics in different display order. In some embodiments, the centralized display may display the same metric for each networked device 204 whose screen content is displayed on the centralized display. For example, if the networked devices 204 in an emergency room are configured to cycle through rate and time, and the networked device 204 in an intensive care unit are configured to cycle through rate and dose, the centralized display configured to display the screen content associated with all of the networked devices 204 in the emergency room and the intensive care unit may cycle through rate, time, and dose for all such networked devices 204 (e.g., a union of the different sets of metrics). In some cases, the centralized display may cycle through all of the available metrics regardless of the characteristics of the individual networked devices 204. Alternatively, the centralized display may not display the same metric for each networked device 204, and cycle through rate and time for the networked devices 204 in the emergency room and cycle through rate and dose for the networked devices 204 in the intensive care unit. In some implementations, the centralize display provides an indication of the CCA associated with the individual metrics displayed on the centralized display. For example, the metrics associated with the networked devices 204 in the emergency room may look different from the metrics associated with the networked devices 204 in the intensive care unit (e.g., in location, in size, in color, based on presence of indicators, etc.). The centralized display may be connected to the server 202, or to another server not illustrated in FIG. 2 that is in network communication with the server 202.

Architecture of Networked Device

Figure 3:
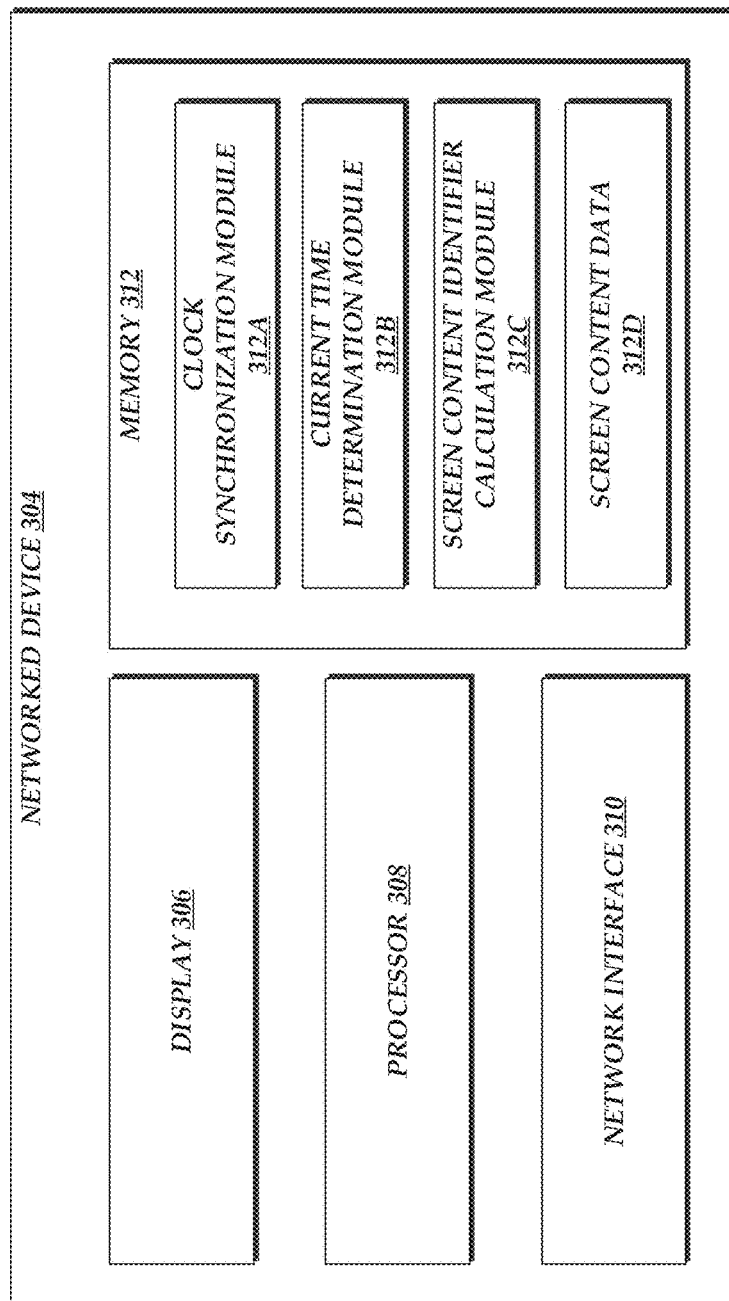
FIG. 3 illustrates a general architecture of an example networked device in accordance with aspects of this disclosure.

With reference to FIG. 3, the components of an example networked device are described in greater detail. The example architecture of the networked device 304 depicted in FIG. 1B includes an arrangement of computer hardware and software modules that may be used to implement aspects of the present disclosure. The networked device 304 may include many more (or fewer) elements and/or subelements than those shown in FIG. 3. It is not necessary, however, that all of these elements be shown in order to provide an enabling disclosure.

As illustrated, the networked device 304 includes a display 306, a processor 308, a network interface 310, and a memory 312, all of which may communicate with one another by way of a communication bus. The display 306 may display information generated or stored by the networked device 304 or any other information associated with the networked device 304. For example, the networked device may be an infusion pump being used to deliver medication to a patient. In such a case, the display 306 may display the volume of the medication infused so far, the volume of the medication to be infused, the rate at which the medication is being infused, and the like. The processor 308 may receive information and instructions from other computing systems or services via a network. The processor 308 may also transmit information to and receive information from the memory 312 and further provide content to the display 306 for display. The network interface 310 may provide connectivity to one or more networks or computing systems in the network environment described herein. For example, the network interface 310 may be a serial port, a parallel port, or any other communication interface that can enable or facilitate wired or wireless communication according to any communication protocols such as Zigbee (e.g., IEEE 802.15.4), Bluetooth, Wi-Fi (e.g., IEEE 802.11), Near Field Communication (NFC), and the like.

The memory 312 may contain computer program instructions (grouped as modules in some embodiments) that the processor 308 can execute in order to implement one or more aspects of the present disclosure. The memory 312 may include RAM, ROM, and/or other persistent, auxiliary, or non-transitory computer-readable media. In some embodiments, the memory 312 stores an operating system that provides computer program instructions for use by the processor 308 in the general administration and operation of the networked device 304. As illustrated in FIG. 3, the memory 312 may include a clock synchronization module 312A, a current time determination module 312B, a screen content identifier calculation module 312C, and screen content data 312D. In some embodiments, the clock synchronization module 312A, the current time determination module 312B, and the screen content identifier calculation module 312C may, when executed by the processor 308, individually or collectively implement various aspects of the present disclosure. Although shown as distinct modules, in some embodiments, the division of the modules into the clock synchronization module 312A, the current time determination module 312B, and the screen content identifier calculation module 312C is logical in nature, and a single software application executing on the networked device 304 may, when executed by the processor 308, perform some or all of the steps described as being performed by the modules. For example, each of the clock synchronization module 312A, the current time determination module 312B, and the screen content identifier calculation module 312C may be part of the screen content manager 206.

The clock synchronization module 312A facilitates synchronization between the server clock 202C and the internal clocks maintained by the individual networked devices 204. The current time determination module 312B facilitates determination of the current time associated with the internal clock 210. For example, the current time determination module 312B may determine the current time indicated by the internal clock 210 maintained and updated by the clock synchronization module 312A. The screen content identifier calculation module 312C facilitates determination of the screen content to be displayed at any given time. For example, the screen content identifier calculation module 312C calculates a screen content identifier based on the current time determined by the current time determination module 312B.

Although not shown in FIG. 3, the networked device 304 may further include one or more input devices such as a touch screen, mechanical buttons, or a voice recognition system. Further, the networked device 304 may include one or more additional storage devices for storing data generated by the networked device 304 or other data utilized in implementing aspects of the present disclosure.

Near View and Far View

Graphical user interfaces for medical devices that display patient and treatment information have improved clinician efficiency when caring for patients. However, a challenge for designing graphical user interfaces is balancing the amount of information displayed with readability and user-friendliness. Presenting too much information may impede the interaction between the user and the device. In some embodiments, two screen modes may be utilized to present more information when the user is interacting with the device in one mode (e.g., "near view"), and to present less information when the user is simply viewing the device from far away (e.g., "far view"). Near view screens may present user interface buttons, fields, and keys to allow the user to input various commands, whereas far view screens may simply show a single metric that the user may be interested in reviewing from far away. Far view screens may be activated after a period of inactivity (e.g., lack of user input) and may cycle through numerous metrics that are relevant to the clinical setting.

Comparison of Synchronized and Non-Synchronized Displays

Figure 4:
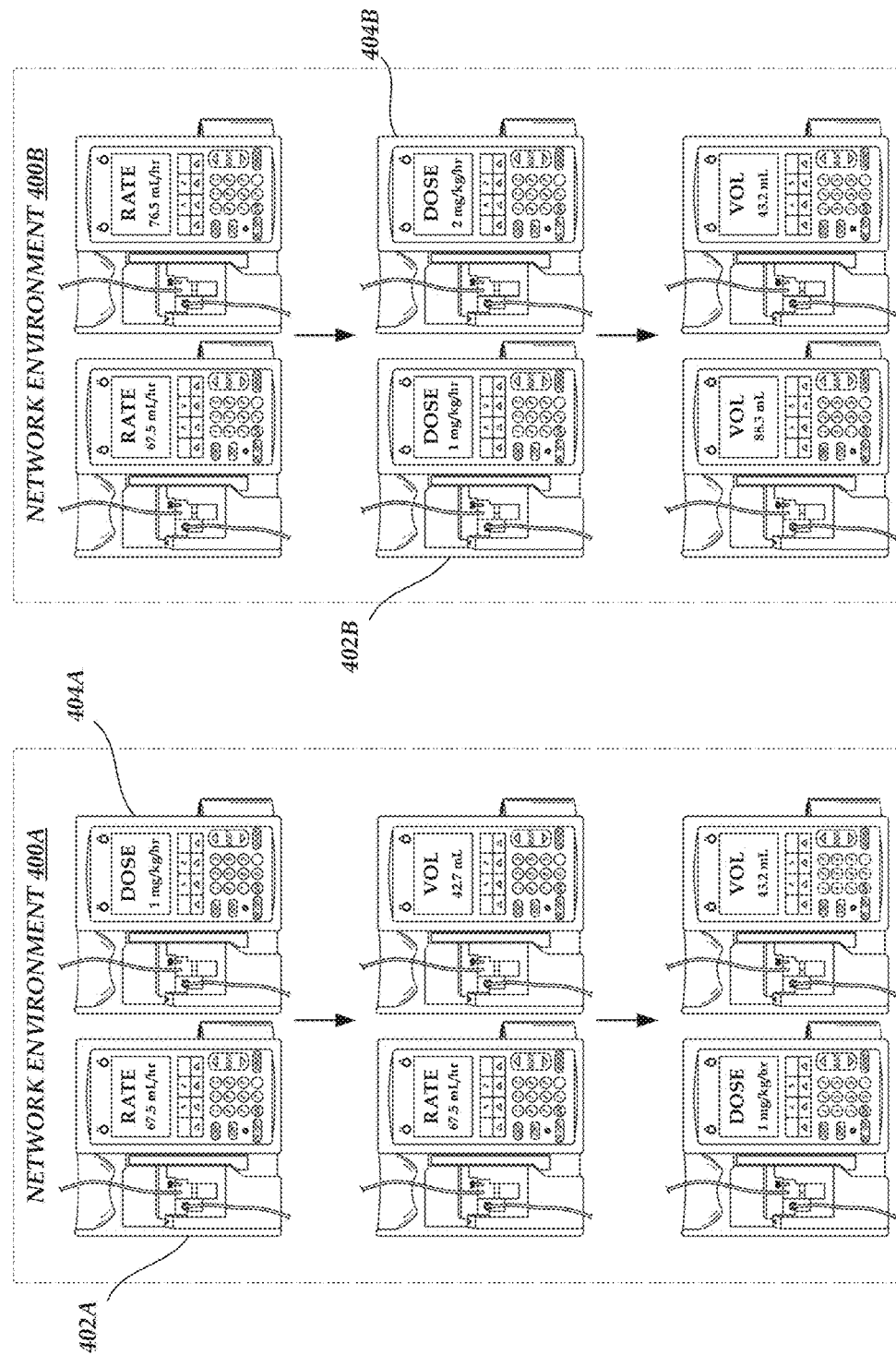
FIG. 4 illustrates example networked devices in network environments in accordance with aspects of this disclosure.

With reference now to FIG. 4, example network environments 400A and 400B will be described. The network environment 400A includes networked devices 402A and 404A that are positioned side by side, and the network environment 400B includes networked devices 402B and 404B that are positioned side by side.

In the top row in FIG. 4, the display of the networked device 402A shows the rate at which the medication is being delivered to the patient, and the display of the networked device 404A shows the time remaining until the medication delivery is finished. As shown, the displays of the networked devices 402A and 404B are not in sync with each other, since the screen content (e.g., the type of metric displayed) of the networked device 402A does not match the screen content (e.g., the type of metric displayed) of the networked device 404A. When the displays of the networked devices are not in sync, it is difficult for the caregiver (e.g., doctor or nurse) to quickly scan the displays and gather relevant information from multiple networked devices, especially if a large number of networked devices are present in the room.

In FIG. 4, the arrows between the rows in FIG. 4 indicate the passage of time (e.g., 1 second, 5 seconds, 1 minute, etc.). After some time has passed, in the middle row, the display of the networked device 402A continues to show the rate, whereas the display of the networked device 404A switches to displaying the volume infused. As illustrated, not only are the two displays out of sync, they also switch at different times.

After some additional time has passed, in the bottom row, the display of the networked device 402A switches to displaying the time remaining, whereas the display of the networked device 404A continues to show the volume infused. When the displays of the networked devices switch to different screen content at different times, it is difficult for the caregiver (e.g., doctor or nurse) to quickly scan the displays and gather relevant information from multiple networked devices, especially if a large number of networked devices are present in the room.

In contrast, as illustrated in FIG. 4, the displays of the networked devices 402B and 404B of the network environment 400B are in sync with each other (e.g., both displaying the rate in the top row, the time remaining in the middle row, and the volume infused in the bottom row). Further, the displays of the networked devices 402B and 404B switch to the next metric at the same time (or at substantially the same time). Thus, the displays of the networked devices 402B and 404B are much easier for a caregiver to scan, especially from afar in a room filled with a large number of such networked devices.

Screen Content Update Method

Figure 5:
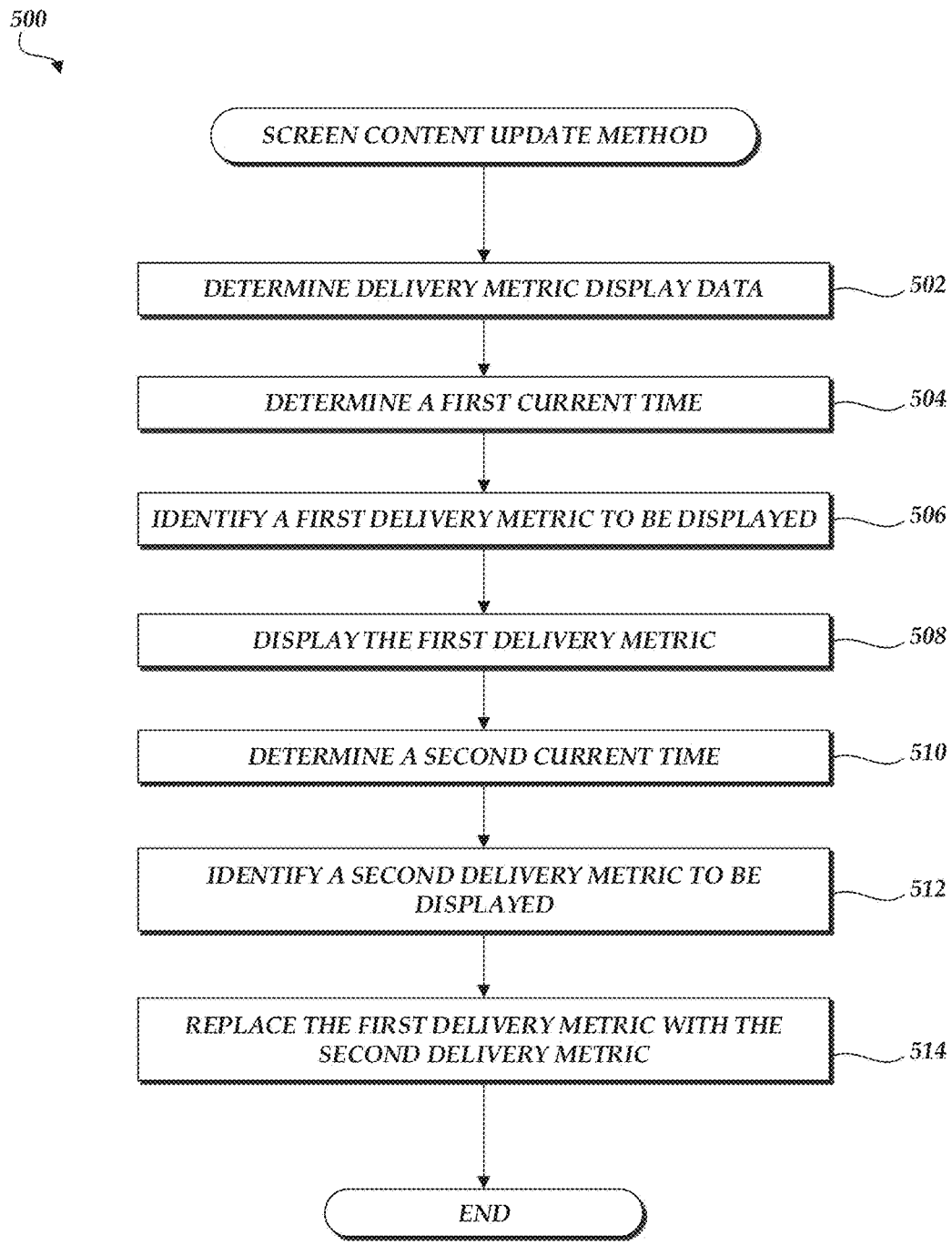
FIG. 5 illustrates an example screen content update method in accordance with aspects of this disclosure.

With reference now to FIG. 5, an example screen content update method 500 will be described. The example method 500 may be carried out, for example, by the networked device 204 of FIG. 2 (or one or more components thereof) or the networked device 304 of FIG. 3 (or one or more components thereof). The method 500 illustrates an example algorithm that may be programmed, using any suitable programming environment or language, to create machine code capable of execution by a CPU or microcontroller of the networked device 204. Various embodiments may be coded using assembly, C, OBJECTIVE-C, C++, JAVA, or other human-readable languages and then compiled, assembled, or otherwise transformed into machine code that can be loaded into read-only memory (ROM), erasable programmable read-only memory (EPROM), or other recordable memory of the networked device 204 that is coupled to the CPU or microcontroller and then then executed by the CPU or microcontroller. For convenience, the steps of the example method 500 are described as being performed by the networked device 204.

At block 502, the networked device 204 determines delivery metric display data from the server 202. The delivery metric display data may include information needed or used to identify the screen content to be displayed on the networked device 204. For example, the delivery metric display data may include the identity and type of delivery metrics to be displayed and the duration for which each delivery metric is to be displayed. In some embodiments, the server 202 has a record of the CCA in which the networked device 204 is located, and the server 202 transmits, based on the CCA associated with the networked device 204, data indicative of which one(s) of the available metrics should be displayed on the networked device 204. For example, the networked device 204 may transmit data indicative of the CCA of the networked device 204 to the server 202 upon entry (e.g., by a caregiver) or detection (e.g., using one or more sensors on the networked device 204) of the CCA. Alternatively, some or all of the delivery metric display data may not be received, and a corresponding default value may be used. For example, if the delivery metric display data received from the server 202 includes an indication of the identity of the delivery metrics to be displayed, but does not include the duration for which each delivery metric is to be displayed, a default value stored on the networked device 204 may be used (e.g., 5 seconds, 10 seconds, or any other value). In some cases, the delivery metric display data may be provided to the networked device 204 by other means such as manual input from a user, copied from a storage device, and so on. The networked device 204 may receive the delivery metric display data from the server 202 according to a predetermined schedule, periodically or aperiodically. In some embodiments, the networked device 204 may receive the delivery metric display data from another source, such as an internal or external storage device or via a manual input from the user of the networked device 204.

At block 504, the networked device 204 determines a first current time based on the internal clock 210. For example, the networked device 204 may determine the current time in response a determination that the screen content should be changed. Such a determination may be made by the networked device 204 in response to detecting a period of inactivity (e.g., when the networked device 204 is switching to screen saver mode). Alternatively or additionally, such a determination may be made by the networked device 204 according to a schedule (e.g., every 5 seconds, every 10 seconds, every minute, etc.). The current time determined using the internal clock 210 may be in the traditional hh:mm:ss format. In other cases, the current time is represented in hours, minutes, seconds, milliseconds, or another unit of time.

At block 506, the networked device 204 identifies a first delivery metric to be displayed on the display of the networked device 204. Identifying the first delivery metric may involve calculating a delivery metric index value and determining the first delivery metric using the delivery metric index value (e.g., by indexing into a list of delivery metrics). For example, if the calculated delivery metric index value is 3, and the list of delivery metrics maintained by the networked device 204 is {dose, rate, volume infused, volume to be infused, time remaining}, the networked device 204 may identify "volume to be infused" as the first delivery metric. Although relevant metrics for an infusion pump are used in this example, any other number and type of metrics, statistics, or information may be cycled through via the display of the networked device 204.

In some embodiments, the delivery metric index value is calculated as follows:

$$\text{(delivery metric index value)} = \text{trunc}((T_{elapsed\_seconds\_in\_system\_time} \bmod (N_{metrics\_available} * T_{display\_period\_length}))/T_{display\_period\_length})$$ Equation (1):

$$\text{(delivery metric index value)} = \text{trunc}((T_{elapsed\_seconds\_in\_system\_time} \bmod (N_{metrics\_available} * T_{display\_period\_length}))/T_{display\_period\_length}) + 1$$ Equation (2):

In Equation (1), $T_{elapsed\_seconds\_in\_system\_time}$ represents the number of seconds elapsed according to the internal clock maintained by the networked device 204, $N_{metrics\_available}$ represents the number of metrics available for display, and $T_{display\_period\_length}$ represents the length of each content display period in seconds.

"trunc" represents the truncation operation, which removes the digits right of the decimal point. For example, trunc (3.5) would equal 3. "mod" represents the modulo operation, which finds the remainder after division of one number by another. For example, 7 mod 3 would equal 1, since 7 divided by 3 would leave a quotient of 2 and a remainder of 1.

Equation (2) is a variation of Equation (1), and the only difference is that 1 is added such that the lowest value of (delivery metric index value) is 1 instead of 0. In Equation (1), "delivery metric index value" of 0 corresponds to the first one of the available metrics, and in Equation (2), "delivery metric index value" of 1 corresponds to the first one of the available metrics.

Although $T_{elapsed\_seconds\_in\_system\_time}$ is used in Equation (1), in some embodiments, the current time used to identify the first delivery metric is not in seconds but in a different unit (e.g., milliseconds, minutes, hours, or some other temporal unit). In some cases, $N_{metrics\_available}$ represents the number of all metrics that the networked device 204 is configured to display. For example, if the networked device 204 is configured to cycle through {dose, rate, volume infused, volume to be infused, time remaining} every time, the networked device 204 may determine that $N_{metrics\_available}$ is equal to 5. In other cases, $N_{metrics\_available}$ represents the number of metrics in a subset that includes some but not all of the metrics that the networked device 204 is configured to display. The metrics in such a subset may be determined based on one or more conditions (e.g., location of the networked device 204, CCA, class or type of medication, or any other parameter associated with the networked device 204). For example, based on a determination that the CCA associated with the networked device 204 is "neonatal intensive care unit" and based on a determination that only {dose, volume infused, volume to be infused} should be displayed for "neonatal intensive care unit," the networked device 204 may determine that the number of metrics in the subset is 3 (e.g., out of 5 metrics). In some embodiments, the networked device 204 downloads the number and type of metrics to be displayed for a given CCA and the length of the content display period for the given CCA from the server 202. Such a download may take place upon the CCA of the networked device 204 being entered or changed by a user of the networked device 204 (e.g., caregiver, administrator, operator, etc.).

Table 1 illustrates example calculations for identifying screen content to be displayed. For this particular networked device 204, three metrics are to be displayed in sequence for 2 seconds each. As shown in Table 1, for the $2000^{th}$ and $2001^{st}$ seconds (e.g., from 2000.00 seconds in system time through 2001.99 in system time), the metric corresponding to an index value of "1" is displayed, for the $2002^{nd}$ and $2003^{rd}$ seconds, the metric corresponding to an index value of "2" is displayed, and for the $2004^{th}$ and $2005^{th}$ seconds, the metric corresponding to an index value of "0" is displayed, and for the $2006^{th}$ and $2007^{th}$ seconds, the metric corresponding to an index value of "1" is displayed again, for the $2008^{th}$ second, the metric corresponding to an index value of "2" is displayed again, and so on. According, in the example of Table 1, three variables (labeled A, B, and C) are used to identify the screen content to be displayed at a given point in time.

TABLE 1

Example calculations for identifying screen content to be displayed

| | | | | | | | | | |
|---|---|---|---|---|---|---|---|---|---|
| A: number of metrics | 3 | | | | | | | | |
| B: content display period (in seconds) | 2 | | | | | | | | |
| C: current time (in seconds) | 2000 | 2001 | 2002 | 2003 | 2004 | 2005 | 2006 | 2007 | 2008 |
| C mod (A * B) | 2 | 3 | 4 | 5 | 0 | 1 | 2 | 3 | 4 |
| (C mod (A * B))/B | 1 | 1.5 | 2 | 2.5 | 0 | 0.5 | 1 | 1.5 | 2 |
| trunc ((C mod (A * B))/B) | 1 | 1 | 2 | 2 | 0 | 0 | 1 | 1 | 2 |

At block 508, the networked device 204 displays the first delivery metric identified at block 506. The display of the first delivery metric may occur at a first time and may continue for the duration (e.g., content display period) specified by the delivery metric display data (or a default duration). Based on the duration for which the first delivery metric is to be displayed, the networked device 204 may perform the following steps such that the display of the delivery metric to be displayed immediately subsequent to the first delivery metric (e.g., the second delivery metric identified at block 512) occurs at a second time that is a specific time period equal to the duration away from the first time at which the first delivery metric was displayed. In some embodiments, none of blocks 504-508 is performed in response to a request, instruction, signal, or communication from the server 202. Alternatively, in some other embodiments, one or more of blocks 504-508 are performed in response to a request, instruction, signal, or communication from the server 202.

At block 510, the networked device 204 determines a second current time based on the internal clock 210. For example, the networked device 204 may determine the current time in response a determination that the screen content should be changed. The determination that the screen content should be changed may be made periodically (e.g., at every second, before each second expires, etc.). In some cases, the networked device 204 may start a timer (e.g., an event timer based on a hardware interrupt or a software interrupt) at the first time at which the first delivery metric is displayed for the duration for which the first delivery metric is to be displayed. When the timer expires, the networked device 204 may determine the second current time. In some cases, the networked device 204 may determine the second current time a specific time period (e.g., 1 second, 5 seconds, or any other time period) before the timer expires. Alternatively, the networked device 204 may set the timer for a duration that is shorter than the duration for which the first delivery metric is to be displayed by a specific time period (e.g., 1 second, 5 seconds, or any other time period). In some cases, the networked device 204 may set the timer at the time of determining the first delivery metric. In some other cases, the networked device 204 may calculate the second current time by adding the duration for which the first delivery metric is to be displayed to the first current time determined at block 504. In such cases, the networked device 204 may determine the current time based on the internal clock 210 once in connection with the initially displayed screen content, and determine the timing of each subsequent screen content by (without accessing the internal clock 210) adding the content display period (e.g., 5 seconds) to the time at which the initially displayed screen content is to be replaced with the next screen content (which can be, for example, 3 seconds from the time the screen content is initially displayed). The networked device 204 may determine the display order based on the predetermined order in which the different screen contents or metrics are arranged (e.g., in the order that the delivery metrics appear in FIG. 7, or in some other order). By not having to re-calculate the display metric index at every second or at every content display period, processing power and other computing resources used to update the screen content can be reduced. Alternatively, by accessing the internal clock 210 at every second or at every content display period, the screen content update process can be more fault-tolerant (e.g., if the networked device 240 for some reason displays the wrong screen content for one content display period, the networked device 240 can still display the correct screen content at the next content display period because the networked device 240 does not rely on any determinations from the previous content display period.)

At block 512, the networked device 204 identifies a second delivery metric to be displayed on the display of the networked device 204. In some embodiments, the networked device 204 determines the second delivery metric using one or more techniques described above in connection with block 506. In other embodiments, the networked device 204 identifies the second delivery metric by determining the next delivery metric in a list that includes all the delivery metrics to be displayed (e.g., cycled through) by networked device 204. For example, in the example illustrated in Table 1, after determining that the delivery metric to be displayed for the $2000^{th}$ second is delivery metric "1", the networked device 204 may determine that the second delivery metric is the next one in the list of delivery metrics (e.g., delivery metric "2" if the list contains more than 2 items, or delivery metric "0" if the list contains only two items).

At block 514, the networked device 204 replaces the first delivery metric displayed on the display with the second delivery metric identified at block 512. Although not illustrated in FIG. 5, blocks 510-514 may be repeated to identify and display additional delivery metrics on the networked device 204. The method 500 may end upon detecting a user input on the networked device 204, upon detecting an error or interrupt routine, upon finishing a given task (e.g., infusion pump finishing the delivery of medication to the patient) or after a predetermined time period. In some embodiments, none of blocks 510-514 is performed in response to a request, instruction, signal, or communication from the server 202. Alternatively, in some other embodiments, one or more of blocks 510-514 are performed in response to a request, instruction, signal, or communication from the server 202.

In the method 500, one or more of the blocks shown in FIG. 5 may be removed (e.g., not performed) and/or the order in which the method 500 is performed may be switched. In some embodiments, additional blocks may be added to the method 500. For example, although not shown in FIG. 5, the networked device 204 may receive reference time information from the server 202 and synchronize its internal clock based on the received information. Although the method 500 is described in the context of displaying delivery metrics, the techniques described herein can be extended to displaying other screen content. The embodiments of the present disclosure are not limited to or by the example shown in FIG. 5, and other variations may be implemented without departing from the spirit of this disclosure.

Examples of Networked Devices

Although some embodiments of the present disclosure are described with respect to infusion pumps, the techniques described herein may be extended to other medical devices or networked devices. For example, one or more networked devices describe herein may be patient care monitors configured to display blood pressure, heart rate, blood oxygenation, and the like. Additionally or alternatively, one or more networked devices described herein may be a smartphone or tablet executing an application configured to display the screen content according to one or more aspects of the present disclosure (e.g., based on an internal clock of the smartphone or tablet and based on parameters received from the server 202 or another centralized server). Displaying such screen content may be synchronized with one or more other networked devices in the network environment.

Synchronized Metric Switching Method

Figure 6:
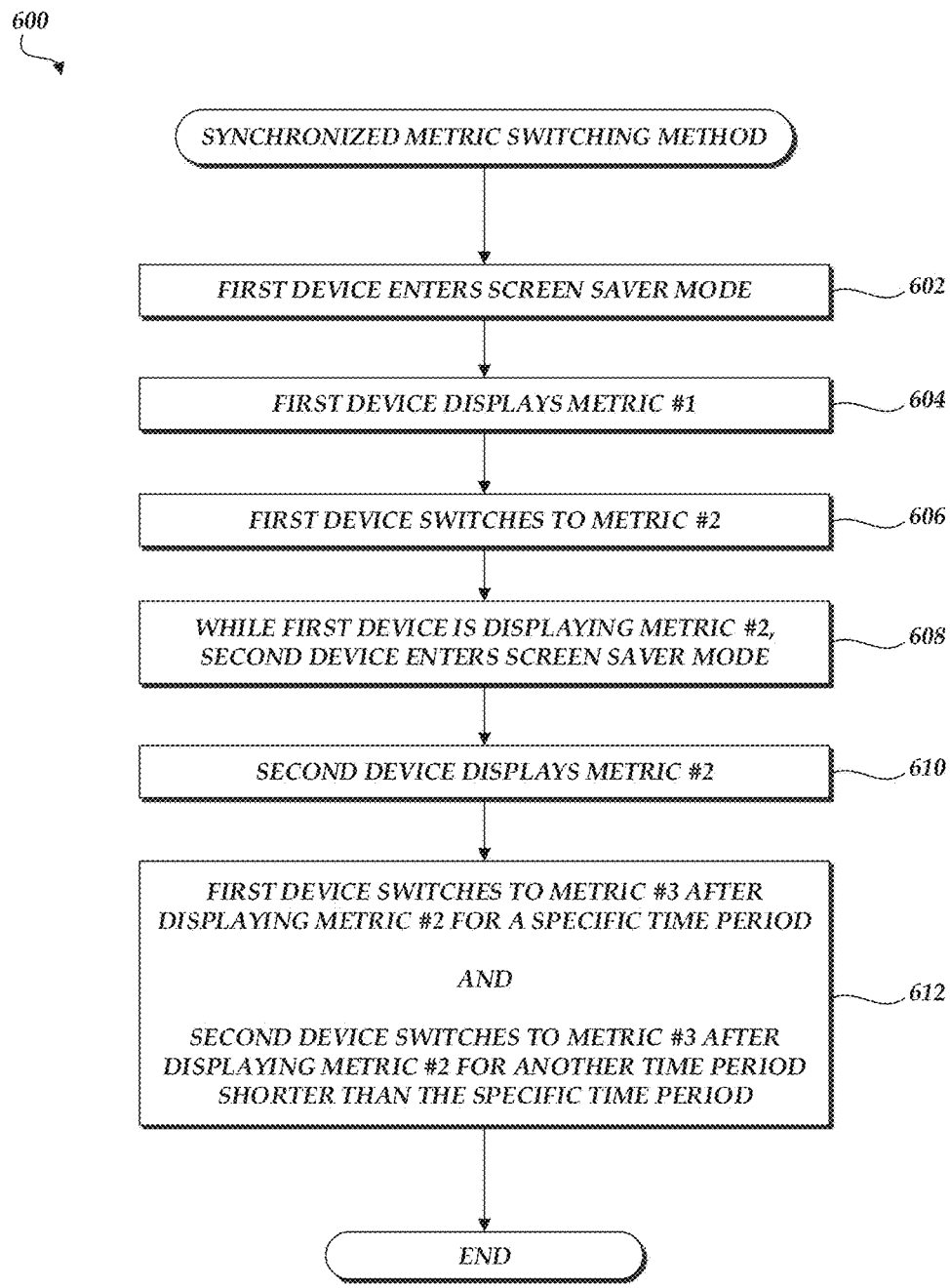
FIG. 6 illustrates an example synchronized metric switching method in accordance with aspects of this disclosure.

With reference now to FIG. 6, an example synchronized metric switching method 600 will be described. The example method 600 may be carried out, for example, by the networked device 204 of FIG. 2 (or one or more components thereof) or the networked device 304 of FIG. 3 (or one or more components thereof). The method 600 illustrates an example algorithm that may be programmed, using any suitable programming environment or language, to create machine code capable of execution by a CPU or microcontroller of the networked device 204. Various embodiments may be coded using assembly, C, OBJECTIVE-C, C++, JAVA, or other human-readable languages and then compiled, assembled, or otherwise transformed into machine code that can be loaded into read-only memory (ROM), erasable programmable read-only memory (EPROM), or other recordable memory of the networked device 204 that is coupled to the CPU or microcontroller and then then executed by the CPU or microcontroller. For convenience, the steps of the example method 600 are described as being performed by the first networked device and/or the second networked device. In some embodiments, the first and second networked devices share one or more characteristics (e.g., CCA, medication, class of medication, patient, network environment, and/or others).

At block 602, the first networked device enters screen saver mode. The first networked device may enter screen saver mode upon detecting inactivity (or no activity) at the first networked device for a specific time period (e.g., inactivity for 1 minute, for 5 minutes, or for any other duration). Inactivity may include not receiving any user input on the first networked device.

At block 604, the first networked device displays metric #1. For example, the first networked device may identify metric #1 using one or more techniques described above in connection with the method 500. The first networked device may determine, upon entering screen saver mode, the current time associated with its internal clock 210, calculate the metric index value associated with the metric to be displayed, and display the identified metric on its display.

At block 606, the first networked device switches to metric #2. For example, the first networked device may identify metric #2 using one or more techniques described above in connection with the method 500, and replace metric #1 with metric #2.

At block 608, while the first networked device is displaying metric #2, the second networked device enters screen saver mode. The second networked device may enter screen saver mode upon detecting inactivity (or no activity) at the second networked device for a specific time period (e.g., inactivity for 1 minute, for 5 minutes, or for any other duration). Inactivity may include not receiving any user input on the second networked device.

At block 610, the second networked device displays metric #2. For example, the second networked device may identify metric #2 using one or more techniques described above in connection with the method 500. The second networked device may determine, upon entering screen saver mode, the current time associated with its internal clock 210, calculate the metric index value associated with the metric to be displayed, and display the identified metric on its display. Even though the first networked device displayed metric #1 after entering screen saver mode, by the time the second networked device has entered screen saver mode, the internal clocks 210 of the first and second networked devices have reached a time period during which metric #2 should be displayed on both of the first and second networked devices. At the time the second networked device displays metric #2, both of the first and second networked devices are displaying metric #2.

At block 612, the first networked device switches to metric #3 after displaying metric #2 for a specific time period (e.g., duration for which the first networked device is configured to display metric #2 or each metric). Further, the second networked device switches to metric #3 after displaying metric #2 for another time period that is shorter than the specific time period for which the first networked device displayed metric #2. In some embodiments, the first networked device and the second networked device do not rely on a signal transmitted by the server 202 to determine when to switch to the next metric and the first networked device and the second networked device do not communicate with each other to synchronize the metric switching. In such embodiments, even without such signal from the server 202 or inter-device communication, the first and second networked devices switch to metric #3 at the same time (or at substantially the same time). Alternatively, in some other embodiments, the first networked device and the second networked device do rely on a signal transmitted by the server 202 to determine when to switch to the next metric and/or the first networked device and the second networked device do communicate with each other to synchronize the metric switching.

In some cases, the time at which the first networked device switches to metric #3 is different from the time at which the second networked device switches to metric #3 due to the difference in the internal clock of the first networked device and the internal clock of the second networked device. For example, the time difference may be a non-zero value that is less than 1 second. In some embodiments, a first time difference between the time at which the first networked device switches to metric #3 and the time at which the second networked device switches to metric #3 is equal to a second time difference between the time at which the first networked device subsequently switches from metric #3 to metric #4 and the time at which the second networked device subsequently switches from metric #3 to metric #4. Alternatively, in some other embodiments, a first time difference between the time at which the first networked device switches to metric #3 and the time at which the second networked device switches to metric #3 is different from a second time difference between the time at which the first networked device subsequently switches from metric #3 to metric #4 and the time at which the second networked device subsequently switches from metric #3 to metric #4 (e.g., due to the internal clocks becoming out of sync with the server clock 202C at different rates). Although not illustrated in FIG. 6, blocks 510-514 of FIG. 5 may be performed by each of the first and second networked devices to identify and display additional metrics.

In the method 600, one or more of the blocks shown in FIG. 6 may be removed (e.g., not performed) and/or the order in which the method 600 is performed may be switched. In some embodiments, additional blocks may be added to the method 600. Although the method 600 is described in the context of screen saver mode, the techniques described herein can be extended to screen content switching in any other mode (e.g., when the networked device is turned on, upon detecting user input indicating that the networked device should begin displaying and cycling through screen content, and so on). The embodiments of the present disclosure are not limited to or by the example shown in FIG. 6, and other variations may be implemented without departing from the spirit of this disclosure.

Example User Interface

Figure 7:
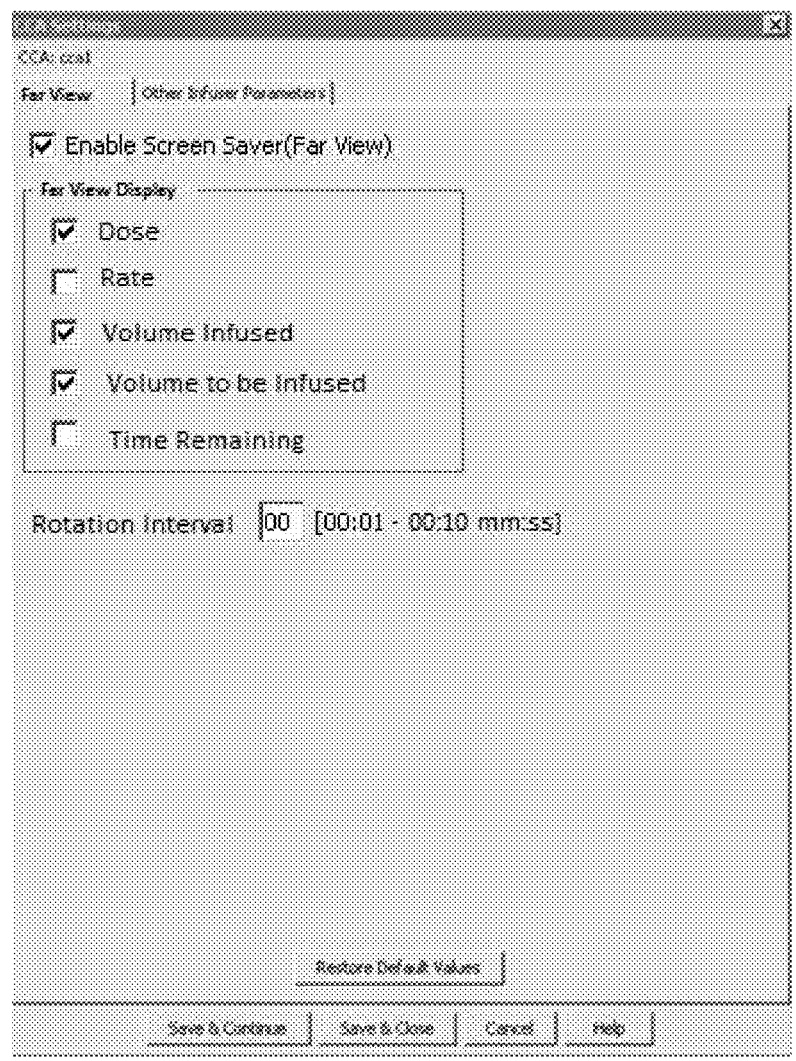
FIG. 7 illustrates an example user interface for specifying the screen content management rules in accordance with aspects of this disclosure.

FIG. 7 illustrates an example user interface 700 for specifying the screen content management rules for a given CCA. As shown, the user interface 700 includes a checkbox for indicating whether screen saver mode is to be enabled for the given CCA, and additional checkboxes for specifying which metrics are to be cycled through in screen saver mode. Further, the user interface 700 includes a field for specifying the content display period (e.g., the duration for which each metric is to be displayed before switching to the next metric). The specified screen content management rules may be transmitted to all of the individual networked devices in the network environment, or only to those associated with the given CCA.

Although the user interface 700 is described in the context of a CCA-specific screen content display scheme, in other embodiments, the screen content display can be specific to one or more other characteristics of the networked device. For example, the number and type of metrics to be cycled through may be drug-specific (e.g., infusion pumps delivering drug "A" may cycle through different type and number of metrics than infusion pumps delivering drug "B"), drug-class-specific (e.g., infusion pumps delivering vasoactive drugs may cycle through different type and number of metrics than infusion pumps delivering anti-infective drugs), CCA-specific (e.g., infusion pumps in operating rooms may cycle through different type and number of metrics than infusion pumps in emergency rooms), patient-specific (e.g., infusion pumps connected to patient "X" may cycle through different type and number of metrics than infusion pumps connected to patient "Y") or any combination-specific such as CCA-drug-specific, CCA-drug-class-specific, and so on (e.g., infusion pumps in operating rooms and delivering vasoactive drugs may cycle through different type and number of metrics than infusion pumps in operating rooms and delivering anti-infective drugs, etc.).

In some embodiments, one or more metrics may not be available for a given drug or drug-class. For example, if the screen content switching is set to be CCA-specific, and networked devices in emergency rooms are configured (e.g., based on the parameters/settings downloaded from the server 202) to cycle through rate, dose, and volume infused. In a particular emergency room, there are two infusion pumps delivering drug "A" and drug "B," respectively. However, if drug "B" cannot be or typically is not administered in a dose-fashion, the infusion pump delivering drug "B" may display the rate for the duration during which the dose is supposed to be displayed. For example, if the screen content switching interval is 10 seconds, the infusion pump delivering drug "A" may display the rate for 10 seconds, the dose for 10 seconds, and the volume infused for 10 seconds and so on. In contrast, the infusion pump delivering drug "B" may display the rate for 20 seconds and the volume infused for 10 seconds and so on (based on the inability to display the dose for drug "B").

Technical Advantages

As described above, in some embodiments, the individual networked devices in the network environment cause their respective screen content to be changed in response to a heartbeat signal received from the server. For example, the server may transmit a heartbeat signal to each networked device every 5 minutes, indicating that the networked device should change the displayed content or display the next content in a given display order. The heartbeat signal may also indicate which content the networked device should display (e.g., by including a content identifier in the heartbeat signal transmitted to the networked device). However, such use of heartbeat signals can consume valuable network resources (e.g., bandwidth) and overwhelm the network, especially if the network includes a large number of such networked devices. Further, processing such heartbeat signals from the server may require a sophisticated processor on the networked device and/or consume valuable processing power. Displaying the screen content based on an internal clock maintained by the individual networked devices and without communicating with the server each time new screen content needs to be displayed, the amount of data transmitted across the network environment may be significantly reduced and valuable network resources and/or processing power can be preserved for other uses.

In other embodiments, the individual networked devices locally store a fixed schedule of which metric to display at what time. In such embodiments, a networked device may store a table that specifies, for each CCA, which metric to display at a given time of day. For example, the table may specify that for networked devices in the ICU should display metric #1 for the first 10 minutes of every hour, metric #2 for the second 10 minutes, metric #3 for the third 10 minutes, and so on, and for networked devices in the OR should display metric #3 for the first 30 minutes of every hour, and metric #4 for the second 30 minutes of every hour. As another example, the table may specify, for each 5-second interval in the 24 hours of a given data, the metric to be displayed for the 5-second interval. However, locally storing such a table would consume a large amount of memory or disk space, which may not be desired for networked devices having limited memory/storage. Also, accessing such a table that is stored remotely over a network can consume valuable network resources (e.g., bandwidth) and overwhelm the network, especially if the network includes a large number of such networked devices. Displaying the screen content based on an internal clock maintained by the individual networked devices and without storing or accessing large amounts of data specifying the screen content to be displayed at any given interval, the amount of storage space needed and/or data transmitted across the network environment may be significantly reduced and valuable storage/network resources can be preserved for other uses.

Example Embodiments

One aspect of the disclosure provides an apparatus configured to deliver medication to patients. The apparatus may include a display, a processor, and a memory. The memory may store an internal clock data according to which one or more delivery metrics are to be displayed on the display. The memory may further store instructions that, when executed by the processor, configure the processor to: receive delivery metric display data from a server in network communication with the apparatus, wherein the delivery metric display data includes a screen change time interval and an indication of one or more delivery metrics to be displayed; in response to a period of inactivity, determine a first current time based on the internal clock data; identify a first delivery metric based on inputting the first current time into a delivery metric determination function, wherein the delivery metric determination function is configured to identify one of a plurality of delivery metrics to be displayed on the display based on the screen change time interval and the indication of the one or more delivery metrics received from the server; cause the first delivery metric to be displayed on the display at a first time; within the screen change time interval from the first time, determine a second current time based on the internal clock data; identify a second delivery metric different from the first delivery metric based on inputting the second current time into the delivery metric determination function; and cause the first delivery metric displayed on the display to be replaced with the second delivery metric at a second time that is not later than the first time by a time period equal to the screen change time.

The apparatus can further include any sub-combination of one or more of the following features: where the instructions, when executed by the processor, further configure the processor to transmit a clock synchronization request to the server, receive a clock synchronization signal from the server, and update the internal clock data based on the clock synchronization signal; where the instructions, when executed by the processor, further configure the processor to transmit the clock synchronization request to the server according to a predefined schedule; where wherein the instructions, when executed by the processor, further configure the processor to determine that a user input has not been received for a threshold amount of time, and in response to the determination that the user input has not been received for the threshold amount of time, determine the first current time based on the internal clock data; where the instructions, when executed by the processor, further configure the processor to calculate a first delivery metric index value based on the first current time and the screen change time interval, and identify the first delivery metric based on the first delivery metric index and the indication of the one or more delivery metrics to be displayed; where the instructions, when executed by the processor, further configure the processor to calculate the first delivery metric index value based on a modulo operation including the screen change time interval and a number of metrics included in the indication of the one or more delivery metrics to be displayed; where the instructions, when executed by the processor, further configure the processor to determine the second current time before an amount of time equal to the screen change time interval has elapsed since the first time; where the instructions, when executed by the processor, further configure the processor to determine the second current time at a time that precedes the second time by a predefined amount of time; where the instructions, when executed by the processor, further configure the processor to within the screen change time interval from the second time, determine a third current time based on the internal clock data, identify a third delivery metric different from the second delivery metric based on inputting the third current time into the delivery metric determination function, and cause the second delivery metric displayed on the display to be replaced with the third delivery metric at a third time that is not later than the second time by the time period equal to the screen change time interval, such that a first time difference between the first time and the second time is shorter than a second time difference between the second time and the third time; and where the second time difference is equal to the screen change time interval, and the first time difference is shorter than the screen change time interval.

One aspect of the disclosure provides a method of providing synchronized screen content. The method may include: receiving, by a networked device in network communication with a server, metric display data from the server, the metric display data including a screen change time interval and an indication of one or more metrics to be displayed; in response to detecting a period of inactivity, determining a first current time associated with an internal clock of the networked device; calculating a first metric index value based on the first current time and the screen change time interval; displaying a first metric associated with the first metric index value on a display of the networked device at a first time; within the screen change time interval from the first time, determining a second current time associated with the internal clock of the networked device; calculating a second metric index value different from the first metric index value based on the second current time; and replacing the first metric displayed on the display of the networked device with a second metric associated with the second metric index value at a second time that is not later than the first time by a time period equal to the screen change time interval.

The method can further include any sub-combination of one or more of the following features: where the method further includes transmitting a clock synchronization request to the server, receiving a clock synchronization signal from the server, and updating the internal clock based on the clock synchronization signal; where the method further includes transmitting the clock synchronization request to the server according to a predefined schedule; where the method further includes determining that a user input has not been received for a threshold amount of time, and in response to determining that the user input has not been received for the threshold amount of time, determining the first current time associated with the internal clock; where the method further includes calculating the first metric index value based on a modulo operation including the screen change time interval and a number of metrics included in the indication of the one or more metrics to be displayed; where the method further includes determining the second current time before an amount of time equal to the screen change time interval has elapsed since the first time; where the method further includes determining the second current time at a time that precedes the second time by a predefined amount of time; where the method further includes, within the screen change time interval from the second time, determining a third current time associated with the internal clock, calculating a third metric index value different from the second metric index value based on the third current time, and replacing the second delivery metric displayed on the display with a third metric associated with the third metric index value at a third time that is not later than the second time by the time period equal to the screen change time interval, such that a first time difference between the first time and the second time is shorter than a second time difference between the second time and the third time; and where the second time difference is equal to the screen change time interval, and the first time difference is shorter than the screen change time interval.

One aspect of the disclosure provides a system adapted to provide synchronized screen content. The system may include a server and a plurality of networked devices in network communication with the server. Each networked device of the plurality of networked devices may be configured to: receive metric display data from the server, the metric display data including a screen change time interval and an indication of one or more metrics to be displayed; in response to a period of inactivity, determine a first current time associated with an internal clock of the networked device; calculate a first metric index value based on the first current time and the screen change time interval; display a first metric associated with the first metric index value on a display of the networked device at a first time; within the screen change time interval from the first time, determine a second current time associated with the internal clock of the networked device; calculate a second metric index value different from the first metric index value based on the second current time; and replace the first metric displayed on the display of the networked device with a second metric associated with the second metric index value at a second time that is not later than the first time by a time period equal to the screen change time interval.

The system can further include any sub-combination of one or more of the following features: where the networked device is further configured to transmit a clock synchronization request to the server, receive a clock synchronization signal from the server, and update the internal clock based on the clock synchronization signal; where the networked device is further configured to transmit the clock synchronization request to the server according to a predefined schedule; where the networked device is further configured to determine that a user input has not been received for a threshold amount of time, and in response to the determination that the user input has not been received for the threshold amount of time, determine the first current time associated with the internal clock; where the networked device is further configured to calculate the first metric index value based on a modulo operation including the screen change time interval and a number of metrics included in the indication of the one or more metrics to be displayed; where the networked device is further configured to determine the second current time before an amount of time equal to the screen change time interval has elapsed since the first time; where the networked device is further configured to determine the second current time at a time that precedes the second time by a predefined amount of time; where the networked device is further configured to, within the screen change time interval from the second time, determine a third current time associated with the internal clock, calculate a third metric index value different from the second metric index value based on the third current time, and replace the second delivery metric displayed on the display with a third metric associated with the third metric index value at a third time that is not later than the second time by the time period equal to the screen change time interval, such that a first time difference between the first time and the second time is shorter than a second time difference between the second time and the third time; and where the second time difference is equal to the screen change time interval, and the first time difference is shorter than the screen change time interval.

One aspect of the disclosure provides a system adapted to provide synchronized screen content. The system may include a server and a plurality of infusion pumps configured to deliver medications to one or more patients and in network communication with the server. Each respective infusion pump of the plurality of infusion pumps networked devices may include (i) a display configured to display one or more metrics of a plurality of metrics maintained by the respective infusion pump and (ii) a memory configured to store internal clock data usable to determine a current time associated with the respective networked device. The respective infusion pump is configured to: receive a clock synchronization data from the server, wherein the clock synchronization data is indicative of a reference time associated with the server; update the internal clock data based on the clock synchronization data; receive metric display data from the server, wherein the metric display data comprises a metric display period and an indication of two or more metrics to be displayed on the display of the respective networked device; based on a determination that a user input has not been received for a threshold amount of time, determine a first current time associated with the internal clock data; calculate a first metric index based on the first current time, the metric display period, and the indication of the two or more metrics received from the server; determine a first metric of the plurality of metrics that is associated with the first metric index; cause the first metric to be displayed on the display of the respective infusion pump at a first time; within at least the metric display period from the first time, determine a second current time associated with the internal clock data; calculate a second metric index based on the second current time, the metric display period, and the indication of the two or more metrics received from the server; determine a second metric of the plurality of metrics that is associated with the second metric index; and cause the first metric displayed on the display of the respective infusion pump to be replaced with the second metric at a second time that is not later than the first time by a time period equal to the metric display period.

The system can further include any sub-combination of one or more of the following features: where the respective infusion pump is further configured to calculate the first metric index value based on a modulo operation comprising a length of the metric display period and a count of the two or more metrics included in the indication received from the server; and where the respective infusion pump is further configured to, within the metric display period from the second time, determine a third current time associated with the internal clock data, calculate a third metric index based on the third current time, the metric display period, and the indication of the two or more metrics received from the server, determine a third metric of the plurality of metrics that is associated with the third metric index, and cause the second metric displayed on the display of the respective infusion pump to be replaced with the third metric at a third time that is not later than the second time by the time period equal to the metric display period, where a first time difference between the first time and the second time is shorter than a second time difference between the second time and the third time.

One aspect of the disclosure provides an apparatus adapted to provide synchronized screen content. The apparatus may include a display, a processor in communication with the display, and a memory storing an internal clock data according to which one or more metrics are to be displayed on the display. The memory may further store instructions that, when executed by the processor, configure the processor to: determine a first current time based on the internal clock data; identify a first one of a plurality of screen contents to be displayed on the display based on (i) the first current time, (ii) a content display period length indicative of a duration for which the first screen content is to be displayed on the display, and (iii) a screen content count indicative of a count of the plurality of screen contents to be displayed on the display; and cause the first screen content to be displayed on the display at a first time for a first duration that is less than or equal to the content display period length.

The apparatus can further include any sub-combination of one or more of the following features: where the instructions, when executed by the processor, further configure the processor to determine that a user input has not been received for a threshold amount of time, in response to the determination that the user input has not been received for the threshold amount of time, determine the first current time based on the internal clock data; where the instructions, when executed by the processor, further configure the processor to calculate a screen content index based on the first current time and the content display period length, and identify the first screen content based on the calculated screen content index; where the instructions, when executed by the processor, further configure the processor to calculate the screen content index based on a modulo operation comprising the content display period length and the screen content count; where the instructions, when executed by the processor, further configure the processor to determine a second current time before an amount of time equal to the content display period length has elapsed since the first time, identify a second one of the plurality of screen contents based on (i) the second current time, (ii) the content display period length, and (iii) the screen content count, cause the second screen content to be displayed on the display at a second time for a second duration that is equal to the content display period length; where the instructions, when executed by the processor, further configure the processor to cause the first screen content and the second screen content to be displayed on the display such that the first duration for which the first screen content is displayed on the display is shorter than the second duration for which the second screen content is displayed on the display; where the instructions, when executed by the processor, further configure the processor to determine the second current time at a time that precedes the second time by a predefined amount of time; where the instructions, when executed by the processor, further configure the processor to receive a clock synchronization data from a server in network communication with the apparatus, and update the internal clock data based on the clock synchronization data; where the instructions, when executed by the processor, further configure the processor to transmit a clock synchronization request to the server according to a predefined schedule.

One aspect of the disclosure provides a method of providing synchronized screen content. The method may include: determining a first current time associated with a medical device based on an internal clock associated with the medical device; identifying a first one of a plurality of screen contents to be displayed on a display of the medical device based on (i) the first current time, (ii) a content display period length indicative of a duration for which the identified screen content is to be displayed on the display, and (iii) a screen content count indicative of a count of the plurality of screen contents to be displayed on the display; and displaying the identified screen content on the display at a first time for a duration that is less than or equal to the content display period length.

The method can further include any sub-combination of one or more of the following features: where the method further includes determining that a user input has not been received for a threshold amount of time, and in response to determining that the user input has not been received for the threshold amount of time, determining the first current time based on the internal clock data; where the method further includes calculating a screen content index based on the first current time and the content display period length, and identifying the first screen content based on the calculated screen content index; where the method further includes calculating the screen content index based on a modulo operation comprising the content display period length and the screen content count; where the method further includes determining a second current time before an amount of time equal to the content display period length has elapsed since the first time, identifying a second one of the plurality of screen contents based on (i) the second current time, (ii) the content display period length, and (iii) the screen content count, displaying the second screen content on the display at a second time for a second duration that is equal to the content display period length; where the method further includes displaying the first screen content and the second screen content such that the first duration for which the first screen content is displayed is shorter than the second duration for which the second screen content is displayed; where the method further includes receiving a clock synchronization data from a server in network communication with the medical device, and updating the internal clock data based on the clock synchronization data; where the method further includes transmitting a clock synchronization request to the server according to a predefined schedule.

Other Considerations

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm elements described in connection with the embodiments disclosed herein can be implemented as electronic hardware, computer software, or combinations of both. To clearly illustrate this interchangeability of hardware and software, various illustrative components, blocks, modules, and elements have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, or algorithm described in connection with the embodiments disclosed herein can be embodied directly in hardware, in a software module stored in one or more memory devices and executed by one or more processors, or in a combination of the two.

A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements, and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Unless otherwise explicitly stated, articles such as "a", "an", or "the" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B, and C" can include a first processor configured to carry out recitation A working in conjunction with a second processor configured to carry out recitations B and C.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments described herein can be implemented within a form that does not provide all of the features and benefits set forth herein, as some features can be used or practiced separately from others. All such modifications and variations are intended to be included herein within the scope of this disclosure. Further, additional embodiments created by combining any two or more features or techniques of one or more embodiments described herein are also intended to be included herein within the scope of this disclosure.

What is claimed is:

1. A system configured to provide synchronized screen content, the system comprising:
    a server; and
    a plurality of infusion pumps configured to deliver medications to one or more patients and in network communication with the server, wherein each respective infusion pump of the plurality of infusion pumps comprises (i) a display configured to display one or more metrics of a plurality of metrics maintained by the respective infusion pump and (ii) a memory configured to store internal clock data usable to determine a current time associated with the respective networked device, wherein the respective infusion pump is configured to:
        receive a clock synchronization data from the server, wherein the clock synchronization data is indicative of a reference time associated with the server;
        update the internal clock data based on the clock synchronization data;
        receive metric display data from the server, wherein the metric display data comprises a metric display period and an indication of two or more metrics to be displayed on the display of the respective networked device;
        based on a determination that a user input has not been received for a threshold amount of time, determine a first current time associated with the internal clock data;
        calculate a first metric index based on the first current time, the metric display period, and the indication of the two or more metrics received from the server;
        determine a first metric of the plurality of metrics that is associated with the first metric index;
        cause the first metric to be displayed on the display of the respective infusion pump at a first time;
        within at least the metric display period from the first time, determine a second current time associated with the internal clock data;
        calculate a second metric index based on the second current time, the metric display period, and the indication of the two or more metrics received from the server;
        determine a second metric of the plurality of metrics that is associated with the second metric index; and
        cause the first metric displayed on the display of the respective infusion pump to be replaced with the second metric at a second time that is not later than the first time by a time period equal to the metric display period.

2. The system of claim 1, wherein the respective infusion pump is further configured to calculate the first metric index value based on a modulo operation comprising a length of the metric display period and a count of the two or more metrics included in the indication received from the server.

3. The system of claim 1, wherein the respective infusion pump is further configured to:
    within the metric display period from the second time, determine a third current time associated with the internal clock data;
    calculate a third metric index based on the third current time, the metric display period, and the indication of the two or more metrics received from the server;

determine a third metric of the plurality of metrics that is associated with the third metric index; and cause the second metric displayed on the display of the respective infusion pump to be replaced with the third metric at a third time that is not later than the second time by the time period equal to the metric display period, wherein a first time difference between the first time and the second time is shorter than a second time difference between the second time and the third time.

4. An apparatus configured to provide synchronized screen content of at least one medical device, the apparatus comprising:

a display;

a processor in communication with the display;

a memory storing an internal clock data according to which one or more metrics are to be displayed on the display, the memory further storing instructions that, when executed by the processor, configure the processor to:

determine a first current time based on the internal clock data;

calculate a first screen content index based on (i) the first current time, (ii) a content display period length indicative of a duration for which a medical device screen content is to be displayed on the display, and (iii) a screen content count indicative of a count of a plurality of medical device screen contents to be displayed on the display;

determine a first one of the plurality of medical device screen contents that is associated with the first screen content index;

cause the first medical device screen content to be displayed on the display at a first time for a first duration that is less than or equal to the content display period length;

determine a second current time before an amount of time equal to the content display period length has elapsed since the first time;

calculate a second screen content index based on (i) the second current time, (ii) the content display period length, and (iii) the screen content count;

determine a second one of the plurality of medical device screen contents that is associated with the second screen content index; and cause the second medical device screen content to be displayed on the display at a second time for a second duration that is equal to the content display period length.

5. The apparatus of claim 4, wherein the instructions, when executed by the processor, further configure the processor to:

determine that a user input has not been received for a threshold amount of time; and in response to the determination that the user input has not been received for the threshold amount of time, determine the first current time based on the internal clock data.

6. The apparatus of claim 4, wherein the instructions, when executed by the processor, further configure the processor to calculate the screen content index based on a modulo operation comprising the content display period length and the screen content count.

7. The apparatus of claim 4, wherein the instructions, when executed by the processor, further configure the processor to cause the first medical device screen content and the second medical device screen content to be displayed on the display such that the first duration for which the first medical device screen content is displayed on the display is shorter than the second duration for which the second medical device screen content is displayed on the display.

8. The apparatus of claim 4, wherein the instructions, when executed by the processor, further configure the processor to determine the second current time at a time that precedes the second time by a predefined amount of time.

9. The apparatus of claim 4, wherein the instructions, when executed by the processor, further configure the processor to:

receive a clock synchronization data from a server in network communication with the apparatus; and update the internal clock data based on the clock synchronization data.

10. The apparatus of claim 9, wherein the instructions, when executed by the processor, further configure the processor to transmit a clock synchronization request to the server according to a predefined schedule.

11. A method of providing synchronized screen content of at least one medical device, the method comprising:

determining a first current time associated with a medical device based on an internal clock associated with the medical device;

calculating a first screen content index based on (i) the first current time, (ii) a content display period length indicative of a duration for which a medical device screen content is to be displayed on the display, and (iii) a screen content count indicative of a count of a plurality of medical device screen contents to be displayed on the display;

determining a first one of the plurality of medical device screen contents that is associated with the first screen content index;

displaying the first medical device screen content on the display at a first time for a duration that is less than or equal to the content display period length;

determining a second current time before an amount of time equal to the content display period length has elapsed since the first time;

calculating a second screen content index based on (i) the second current time, (ii) the content display period length, and (iii) the screen content count;

determining a second one of the plurality of medical device screen contents that is associated with the second screen content index; and displaying the second medical device screen content on the display at a second time for a second duration that is equal to the content display period length.

12. The method of claim 11, further comprising:

determining that a user input has not been received for a threshold amount of time; and in response to determining that the user input has not been received for the threshold amount of time, determining the first current time based on the internal clock data.

13. The method of claim 11, further comprising calculating the screen content index based on a modulo operation comprising the content display period length and the screen content count.

14. The method of claim 11, further comprising displaying the first medical device screen content and the second medical device screen content such that the first duration for which the first medical device screen content is displayed is shorter than the second duration for which the second medical device screen content is displayed.

15. The method of claim 11, further comprising:
receiving a clock synchronization data from a server in network communication with the medical device; and
updating the internal clock data based on the clock synchronization data.

16. The method of claim 15, further comprising transmitting a clock synchronization request to the server according to a predefined schedule.

\* \* \* \* \*

UNITED STATES PATENT AND TRADEMARK OFFICE
CERTIFICATE OF CORRECTION

| | |
|---|---|
| PATENT NO. | : 10,089,055 B1 |
| APPLICATION NO. | : 15/861204 |
| DATED | : October 2, 2018 |
| INVENTOR(S) | : Marshall Fryman |

It is certified that error appears in the above-identified patent and that said Letters Patent is hereby corrected as shown below:

On the Title Page

Item (72), Inventor at Line 1, Change "Lidenhurst, IL" to --Lindenhurst, IL--.

Signed and Sealed this
Third Day of September, 2019

Andrei Iancu
*Director of the United States Patent and Trademark Office*